United States Patent
Touge et al.

(10) Patent No.: US 9,745,229 B2
(45) Date of Patent: Aug. 29, 2017

(54) METHOD FOR PRODUCING OPTICALLY ACTIVE COMPOUND, AND NOVEL METAL-DIAMINE COMPLEX

(71) Applicant: TAKASAGO INTERNATIONAL CORPORATION, Tokyo (JP)

(72) Inventors: Taichiro Touge, Hiratsuka (JP); Hideki Nara, Fujisawa (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

(21) Appl. No.: 15/117,333

(22) PCT Filed: Feb. 13, 2015

(86) PCT No.: PCT/JP2015/054017
§ 371 (c)(1),
(2) Date: Aug. 8, 2016

(87) PCT Pub. No.: WO2015/122502
PCT Pub. Date: Aug. 20, 2015

(65) Prior Publication Data
US 2016/0347678 A1    Dec. 1, 2016

(30) Foreign Application Priority Data
Feb. 14, 2014 (JP) ................. 2014-026161

(51) Int. Cl.
| | | |
|---|---|---|
| C07F 15/00 | (2006.01) |
| C07B 53/00 | (2006.01) |
| C07D 215/06 | (2006.01) |
| C07C 213/02 | (2006.01) |
| C07C 217/84 | (2006.01) |
| C07D 241/42 | (2006.01) |
| C07D 265/36 | (2006.01) |
| C07D 209/08 | (2006.01) |
| C07D 209/80 | (2006.01) |
| C07C 303/40 | (2006.01) |
| C07C 311/18 | (2006.01) |
| B01J 31/18 | (2006.01) |
| C07B 31/00 | (2006.01) |
| C07D 209/86 | (2006.01) |
| C07D 209/94 | (2006.01) |

(52) U.S. Cl.
CPC .......... C07B 53/00 (2013.01); B01J 31/1805 (2013.01); C07B 31/00 (2013.01); C07C 213/02 (2013.01); C07C 217/84 (2013.01); C07C 303/40 (2013.01); C07C 311/18 (2013.01); C07D 209/08 (2013.01); C07D 209/80 (2013.01); C07D 209/86 (2013.01); C07D 209/94 (2013.01); C07D 215/06 (2013.01); C07D 241/42 (2013.01); C07D 265/36 (2013.01); C07F 15/0033 (2013.01); C07F 15/0046 (2013.01); B01J 2231/641 (2013.01); B01J 2531/821 (2013.01); B01J 2531/827 (2013.01)

(58) Field of Classification Search
CPC ...................................................... C07F 15/00
USPC .............................................................. 556/137
See application file for complete search history.

(56) References Cited

U.S. PATENT DOCUMENTS 8,404,879 B2 * 3/2013 Touge .................. B01J 31/1805
556/12

FOREIGN PATENT DOCUMENTS

| EP | 2 275 427 A1 | 1/2011 |
| JP | 2001-104795 | * 4/2001 |

OTHER PUBLICATIONS

Dub et al., A Practical Asymmetric Conjugate Addition to Cyclic Enones With Chiral Bifunctional Ru Amido Catalysts, Tetrahedron Letters, vol. 53, No. 27, pp. 3452-3455, 2012.*
Heiden et al., Proton-Assisted Activation of Dihydrogen: Mechanistic Aspects of Proton-Catalyzed Addition of H2 to Ru and Ir Amido Complexes, Journal of the American Chemical Society, vol. 131, No. 10, pp. 3593-3600, 2009.*
Koike et al., Synthesis and Properties of Alkylruthenium Complexes Bearing Primary and Secondary Amine Ligands, Journal of Organometallic Chemistry, vol. 692, No. (1-3), pp. 408-419, 2007.*
Koike et al., Mechanistic Aspects of Formation of Chiral Ruthenium Hydride Complexes from 16-Electron Ruthenium Amide Complexes and Formic Acid: Facile Reversible Decarboxylation and Carboxylation, Advanced Synthesis & Catalysis, vol. 346, No. 1, pp. 37-41, 2004.*
Grazia Zassinovich et al., "Asymmetric Hydrogen Transfer Reactions Promoted by Homogeneous Transition Metal Catalysts", Chem. Rev., 1992, pp. 1051-1069, vol. 92.
Shohei Hashiguchi et al., "Asymmetric Transfer Hydrogenation of Aromatic Ketones Catalyzed by Chiral Ruthenium(II) Complexes", J. Am. Chem. Soc., 1995, pp. 7562-7563, vol. 117.
Akio Fujii et al., "Ruthenium(II)-Catalyzed Asymmetric Transfer Hydrogenation of Ketones Using a Formic Acid-Triethylamine Mixture", J. Am. Chem. Soc., 1996, pp. 2521-2522, vol. 118.
Nobuyuki Uematsu et al., "Asymmetric Transfer Hydrogenation of Imines", J. Am. Chem. Soc., 1996, pp. 4916-4917, vol. 118.
Tianli Wang et al., "Highly Enantioselective Hydrogenation of Quinolines Using Phosphine-Free Chiral Cationic Ruthenium Catalysts: Scope, Mechanism, and Origin of Enantioselectivity", J. Am. Chem. Soc., 2011, pp. 9878-9891, vol. 133.

(Continued)

Primary Examiner — Brenda Coleman
(74) Attorney, Agent, or Firm — Sughrue Mion, PLLC

(57) ABSTRACT

The present invention pertains to a method for producing an optically active compound which includes a step for reducing an imino group of an imine compound or a step for reducing an unsaturated bond of a heterocyclic compound, while in the presence of hydrogen gas as a hydrogen donor and one or more types of complexes selected from a group consisting of a complex represented by general formula (1), a complex represented by general formula (2), a complex represented by general formula (3), and a complex represented by general formula (4) (the general formulas (1)-(4) are as stipulated by claim 1).

3 Claims, No Drawings

(56) References Cited

OTHER PUBLICATIONS

Zi-Yuan Ding et al., "Asymmetric Hydrogenation of 2,4-Disubstituted 1,5-Benzodiazepines Using Cationic Ruthenium Diamine Catalysts: An Unusual Achiral Counteranion Induced Reversal of Enantioselectivity", Angew. Chem. Int. Ed., 2012, pp. 5706-5710, vol. 51.
Takeshi Ohkuma et al., "The Hydrogenation/Transfer Hydrogenation Network: Asymmetric Hydrogenation of Ketones with Chiral $\eta^6$-Arene/N-Tosylethylenediamine-Ruthenium(II) Catalysts", J. Am. Chem. Soc., 2006, pp. 8724-8725, vol. 128.
Karl-Josef Haack et al., "The Catalyst Precursor, Catalyst, and Intermediate in the $Ru^8$—Promoted Asymmetric Hydrogen Transfer between Alcohols and Ketones", Angew. Chem. Int. Ed. Engl., 1997, pp. 285-288, vol. 36 , No. 3.
Jose E. D. Martins et al., "Ru(II) Complexes of N-Alkylated TsDPEN Ligands in Asymmetric Transfer Hydrogenation of Ketones and Imines", Organic Letters, 2009, pp. 847-850, vol. 11, No. 4.
International Searching Authority, International Search Report of PCT/JP2015/054017 dated Apr. 21, 2015 [PCT/ISA/210].
European Patent Office; Communication dated Jun. 14, 2017 from the in counterpart application No. 15748864.4.
Zi-Yuan Ding et al., "Highly Enantioselective Synthesis of Chiral Tetrahydroquinolines and Tetrahydroisoquinolines by Ruthenium-Catalyzed Asymmetric Hydrogenation in Ionic Liquid", Advanced Synthesis & Catalyst, vol. 355, No. 18, Dec. 6, 2013, pp. 3727-2735, (9 pages total).

* cited by examiner

METHOD FOR PRODUCING OPTICALLY ACTIVE COMPOUND, AND NOVEL METAL-DIAMINE COMPLEX

CROSS REFERENCE TO RELATED APPLICATIONS

This application is a National Stage of International Application No. PCT/JP2015/054017, filed Feb. 13, 2015, claiming priority based on Japanese Patent Application No. 2014-026161, filed Feb. 14, 2014, the contents of all of which are incorporated herein by reference in their entirety.

TECHNICAL FIELD

The present invention relates to a method for selectively producing an optically active compound important as a precursor for synthesis of pharmaceuticals and functional materials, the methods using any of a ruthenium-diamine complex, an iridium-diamine complex, and a rhodium-diamine complex as a catalyst.

BACKGROUND ART

In the field of production of optically active amines, many asymmetric reactions, including asymmetric reduction, have been developed, and many asymmetric reactions have been reported which use asymmetric metal complexes having optically active phosphine ligands. Meanwhile, for example, there are many documents reporting that complexes in each of which an optically active nitrogen compound is coordinated to a transition metal, such as ruthenium, rhodium, or iridium, have excellent performance as catalysts for asymmetric synthesis reactions (see Chem Rev. (1992), p. 1051, J. Am. Chem. Soc. 117 (1995), p. 7562, J. Am. Chem. Soc. 118 (1996), p. 2521, and J. Am. Chem. Soc. 118 (1996), p. 4916). Especially, synthesis of optically active amines by hydrogenation reaction has been reported recently (see J. Am. Chem. Soc. 133 (2011), p. 9878, and Angew. Chem. Int. Ed 51 (2012), p. 5706).

However, the conventional asymmetric synthesis methods using these complexes may result in insufficient catalytic activity or insufficient enantiomeric excesses, when certain reaction substrates are used. Hence, further development of such a complex has been demanded. Wills et al. have reported a complex in which the nitrogen atom in one of the diamine moieties is methylated. However, the reaction is limited to the hydrogen transfer reaction, and the element coordinated to ruthenium is a halogen (see Organic Letters (2009) vol. 11, No. 4, p 847).

SUMMARY OF INVENTION

Technical Problems

An object of the present invention is to provide a method for producing an optically active compound, the method using, in a hydrogenation reaction, an asymmetric reduction catalyst comprising a metal complex which is excellent in catalytic activity and enantiomeric excess.

Solution to Problems

To achieve the above-described object, the present inventors have conducted intensive studies, and consequently have found that specific ruthenium, iridium, and rhodium complexes achieve high catalytic activity and excellent enantiomeric excess in reduction reactions using hydrogen gas as a hydrogen source. This finding has led to the completion of the present invention.

Specifically, the present invention includes the following contents.

A method for producing an optically active compound, comprising the step of:

reducing an imino group of an imine compound or reducing an unsaturated bond of a heterocyclic compound in the presence of at least one complex selected from complexes represented by general formula (1) below, complexes represented by general formula (2) below, complexes represented by general formula (3) below, and complexes represented by general formula (4) below and of hydrogen gas serving as a hydrogen donor:

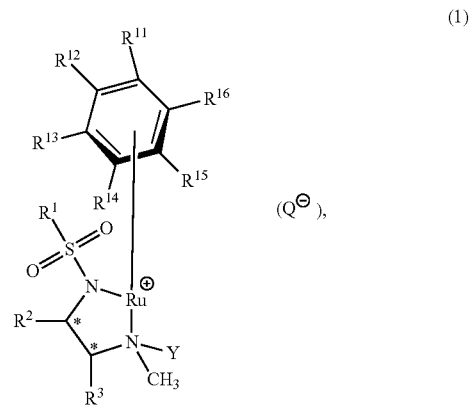

(1)

wherein

* indicates an asymmetric carbon atom, $R^1$ represents a group selected from alkyl groups having 1 to 10 carbon atoms, halogenated alkyl groups having 1 to 10 carbon atoms, and aryl groups having 6 to 30 carbon atoms, wherein said aryl groups may have one or more substituents selected from alkyl groups having 1 to 10 carbon atoms, halogenated alkyl groups having 1 to 10 carbon atoms, and halogen atoms, $R^2$ and $R^3$ each independently represent a group selected from alkyl groups having 1 to 10 carbon atoms, phenyl groups, and cycloalkyl groups having 3 to 8 carbon atoms, wherein said phenyl groups may have one or more substituents selected from alkyl groups having 1 to 10 carbon atoms, alkoxy groups having 1 to 10 carbon atoms, and halogen atoms, and wherein said cycloalkyl groups may have one or more substituents selected from alkyl groups having 1 to 10 carbon atoms, or $R^2$ and $R^3$ form a ring together with the carbon atoms to which $R^2$ and $R^3$ are bonded, Y represents a hydrogen atom or a deuterium atom, $R^{11}$, $R^{12}$, $R^{13}$, $R^{14}$, $R^{15}$, and $R^{16}$ each independently represent a group selected from a hydrogen atom, alkyl groups having 1 to 10 carbon atoms, silyl groups having 1 to 3 alkyl groups having 1 to 10 carbon atoms, alkoxy groups having 1 to 10 carbon atoms, and $—C(=O)—OR^{22}$, wherein $R^{22}$ represents an alkyl group having 1 to 10 carbon atoms, a heteroaryl group having 4 to 10 carbon atoms, or an aryl group having 6 to 10 carbon atoms, and $Q^-$ represents a counter anion;

A ruthenium complex represented by general formula (1):

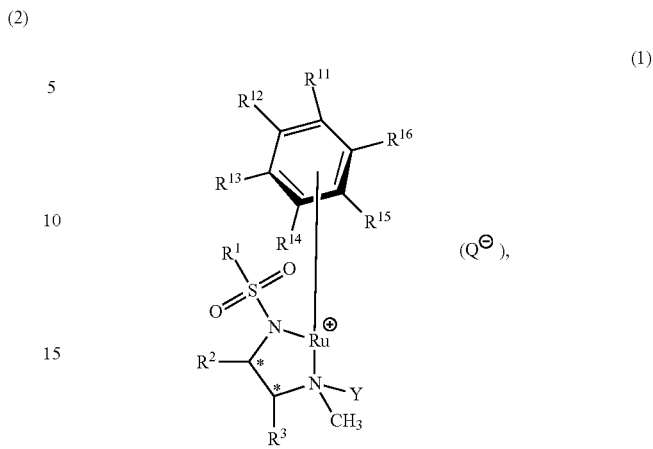

wherein
* indicates an asymmetric carbon atom,
$R^1$ represents a group selected from alkyl groups having 1 to 10 carbon atoms, halogenated alkyl groups having 1 to 10 carbon atoms, and aryl groups having 6 to 30 carbon atoms, wherein said aryl groups may have one or more substituents selected from alkyl groups having 1 to 10 carbon atoms, halogenated alkyl groups having 1 to 10 carbon atoms, and halogen atoms,
$R^2$ and $R^3$ each independently represent a group selected from alkyl groups having 1 to 10 carbon atoms, phenyl groups, and cycloalkyl groups having 3 to 8 carbon atoms, wherein said phenyl groups may have one or more substituents selected from alkyl groups having 1 to 10 carbon atoms, alkoxy groups having 1 to 10 carbon atoms, and halogen atoms, and wherein said cycloalkyl groups may have one or more substituents selected from alkyl groups having 1 to 10 carbon atoms, or $R^2$ and $R^3$ form a ring together with the carbon atoms to which $R^2$ and $R^3$ are bonded,
Y represents a hydrogen atom or a deuterium atom,
$R^{11}$, $R^{12}$, $R^{13}$, $R^{14}$, $R^{15}$, and $R^{16}$ each independently represent a group selected from a hydrogen atom, alkyl groups having 1 to 10 carbon atoms, silyl groups having 1 to 3 alkyl groups having 1 to 10 carbon atoms, alkoxy groups having 1 to 10 carbon atoms, and —C(=O)—OR$^{22}$, wherein R$^{22}$ represents an alkyl group having 1 to 10 carbon atoms, a heteroaryl group having 4 to 10 carbon atoms, or an aryl group having 6 to 10 carbon atoms, and
Q$^-$ represents a counter anion.

An iridium or rhodium complex represented by general formula (4):

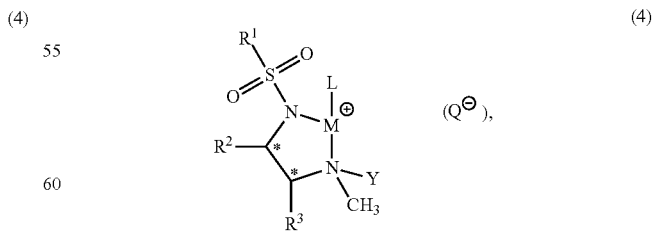

wherein
* indicates an asymmetric carbon atom,
$R^1$ represents a group selected from alkyl groups having 1 to 10 carbon atoms, halogenated alkyl groups having 1 to

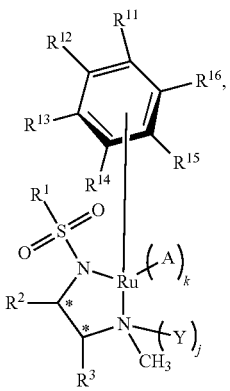

wherein
* indicates an asymmetric carbon atom, and
$R^1$, $R^2$, $R^3$, $R^{11}$, $R^{12}$, $R^{13}$, $R^{14}$, $R^{15}$, $R^{16}$, and Y are as defined above,
A represents a group selected from a trifluoromethanesulfonyloxy group, a p-toluenesulfonyloxy group, a methanesulfonyloxy group, a benzenesulfonyloxy group, a hydrogen atom, a deuterium atom, and halogen atoms, and
j and k each represent 0 or 1, provided that j+k is not 1;

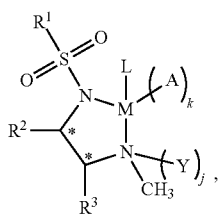

wherein
* indicates an asymmetric carbon atom,
$R^1$, $R^2$, $R^3$, A, and Y are as defined above,
M represents iridium or rhodium,
L represents a cyclopentadienyl or pentamethylcyclopentadienyl ligand, and
j and k each represent 0 or 1, provided that j+k is not 1;

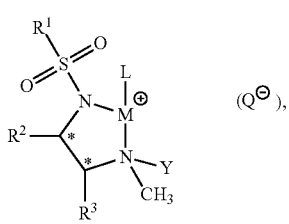

wherein
* indicates an asymmetric carbon atom, and
$R^1$, $R^2$, $R^3$, Y, M, L, and Q$^-$ are as defined above.

10 carbon atoms, and aryl groups having 6 to 30 carbon atoms, wherein said aryl groups may have one or more substituents selected from alkyl groups having 1 to 10 carbon atoms, halogenated alkyl groups having 1 to 10 carbon atoms, and halogen atoms, R² and R³ each independently represent a group selected from alkyl groups having 1 to 10 carbon atoms, phenyl groups, and cycloalkyl groups having 3 to 8 carbon atoms, wherein said phenyl groups may have one or more substituents selected from alkyl groups having 1 to 10 carbon atoms, alkoxy groups having 1 to 10 carbon atoms, and halogen atoms, and wherein said cycloalkyl groups may have one or more substituents selected from alkyl groups having 1 to 10 carbon atoms, or R² and R³ form a ring together with the carbon atoms to which R² and R³ are bonded, Y represents a hydrogen atom or a deuterium atom, M represents iridium or rhodium, L represents a cyclopentadienyl or pentamethylcyclopentadienyl ligand, and Q⁻ represents a counter anion.

The present invention also relates to an asymmetric reduction catalyst comprising the complex represented by general formula (1) or (4).

Advantageous Effects of Invention

According to the present invention, the use, as a catalyst, of the metal complex having the specific diamine compound as a ligand makes it possible to carry out an asymmetric reduction reaction (hydrogenation reaction) of an imine compound or a heterocyclic compound by using hydrogen gas as a hydrogen source.

In comparison with conventional complexes, such as, for example, RuOTf(Tsdpen) (p-cymene) and RuBF₄ (Tsdpen) (p-cymene) complexes which are reported in J. Am. Chem. Soc., 2006, 128, p. 8724 etc. and which have been widely used for reduction of unsaturated bonds of heterocyclic compounds or various C=N bonds until now, the ruthenium complexes, the iridium complexes, and the rhodium complexes of the present invention exhibit high activities and achieve high selectivities in reduction reactions using similar substrates and using hydrogen gas as a hydrogen source, and hence are useful as catalysts for asymmetric reduction. Note that Tsdpen represents N-(p-toluenesulfonyl)-1,2-diphenylethylenediamine.

By conducting a reduction reaction by using the ruthenium complex, the iridium complex, or the rhodium complex of the present invention, it is possible to selectively produce an optically active compound useful as, for example, a raw material for producing pharmaceuticals and functional materials.

DESCRIPTION OF EMBODIMENTS

First, complexes represented by general formulae (1) to (4) used in a method for producing an optically active compound of the present invention are described in detail.

<Ruthenium Complex (Complex Represented by General Formula (1))>

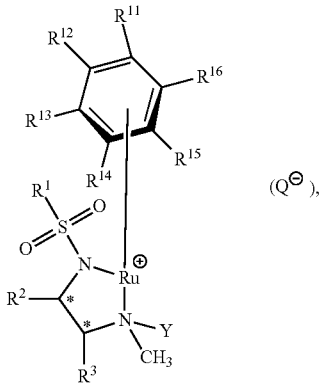

(1)

wherein * indicates an asymmetric carbon atom.

In formula (1), R¹ represents a group selected from alkyl groups having 1 to 10 carbon atoms, halogenated alkyl groups having 1 to 10 carbon atoms, and aryl groups having 6 to 30 carbon atoms, wherein said aryl groups may have one or more substituents selected from alkyl groups having 1 to 10 carbon atoms, halogenated alkyl groups having 1 to 10 carbon atoms, and halogen atoms. R¹ in formula (1) is preferably an aryl group having 6 to 15 carbon atoms and being substituted with 1 to 3 alkyl groups having 1 to 10 carbon atoms, and is more preferably a phenyl group substituted with 1 to 3 alkyl groups having 1 to 3 carbon atoms.

The alkyl group having 1 to 10 carbon atoms represented by R¹ in formula (1) is preferably a linear or branched alkyl group having 1 to 5 carbon atoms. Specific examples of the alkyl group having 1 to 10 carbon atoms include a methyl group, an ethyl group, a n-propyl group, an isopropyl group, a n-butyl group, an isobutyl group, a s-butyl group, a t-butyl group, a n-pentyl group, a n-hexyl group, a n-heptyl group, a n-octyl group, a n-nonyl group, a n-decyl group, and the like. The alkyl group is preferably a methyl group, an ethyl group, a n-propyl group, an isopropyl group, a n-butyl group, an isobutyl group, a s-butyl group, a t-butyl group, or a n-pentyl group.

The halogenated alkyl group having 1 to 10 carbon atoms represented by R¹ in formula (1) is a group which is the same as the above-described alkyl group having 1 to 10 carbon atoms, except that one or multiple hydrogen atoms are replaced by halogen atoms. The halogenated alkyl group having 1 to 10 carbon atoms is preferably a linear or branched halogenated alkyl group having 1 to 5 carbon atoms. Examples of the halogen atoms include chlorine atoms, bromine atoms, fluorine atoms, and the like. Specific examples of the halogenated alkyl group having 1 to 10 carbon atoms include a trifluoromethane group, a trichloromethane group, a tribromomethane group, and the like.

The aryl group having 6 to 30 carbon atoms represented by R¹ in formula (1) may be an aromatic monocyclic group having 6 to 30 carbon atoms, an aromatic polycyclic group having 6 to 30 carbon atoms, or an aromatic fused cyclic group having 6 to 30 carbon atoms. The aryl group having 6 to 30 carbon atoms is preferably an aromatic monocyclic group having 6 to 15 carbon atoms, an aromatic polycyclic group having 6 to 15 carbon, or an aromatic fused cyclic group having 6 to 15 carbon, and is particularly preferably an aromatic monocyclic group having 6 to 12 carbon atoms.

Specific examples of the aryl group having 6 to 30 carbon atoms include a phenyl group, a naphthyl group, an anthryl group, a phenanthryl group, an indenyl group, and the like, and a phenyl group is the most preferable.

In addition, the aryl group represented by $R^1$ in formula (1) optionally has one or more substituents selected from alkyl groups having 1 to 10 carbon atoms, halogenated alkyl groups having 1 to 10 carbon atoms, and halogen atoms.

The alkyl groups and the halogenated alkyl groups serving as the substituents can be selected from the groups defined as the alkyl groups and halogenated alkyl groups represented by $R^1$ in formula (1) described above. Of these groups, linear or branched alkyl groups having 1 to 5 carbon atoms are particularly preferable. Examples of the halogen atoms include chlorine atoms, bromine atoms, fluorine atoms, and the like.

Specific examples of the aryl group represented by $R^1$ in formula (1) and substituted with one or more of the substituents include a p-tolyl group, a 2,4,6-trimethylphenyl group, a 2,4,6-triisopropylphenyl group, a 4-trifluoromethylphenyl group, a pentafluorophenyl group, and the like.

In formula (1), $R^2$ and $R^3$ each independently represent a group selected from alkyl groups having 1 to 10 carbon atoms, phenyl groups, and cycloalkyl groups having 3 to 8 carbon atoms, wherein said phenyl groups may have one or more substituents selected from alkyl groups having 1 to 10 carbon atoms, alkoxy groups having 1 to 10 carbon atoms, and halogen atoms, and wherein said cycloalkyl groups may have one or more substituents selected from alkyl groups having 1 to 10 carbon atoms. Alternatively, $R^2$ and $R^3$ in formula (1) may form a ring together with the carbon atoms to which $R^2$ and $R^3$ are bonded, and preferably forms a cycloalkane together with the carbon atoms to which $R^2$ and $R^3$ are bonded. $R^2$ and $R^3$ in formula (1) is each independently preferably a phenyl group, provided that the phenyl group optionally has one or more substituents selected from alkyl groups having 1 to 10 carbon atoms, alkoxy groups having 1 to 10 carbon atoms, and halogen atoms.

The alkyl group having 1 to 10 carbon atoms represented by each of $R^1$ and $R^3$ in formula (1) can be selected from the groups defined as the alkyl groups having 1 to 10 carbon atoms represented by $R^1$.

Meanwhile, the phenyl group represented by each of $R^2$ and $R^3$ in formula (1) optionally has one or more substituents selected from alkyl groups having 1 to 10 carbon atoms, alkoxy groups having 1 to 10 carbon atoms, and halogen atoms.

The alkyl groups serving as the substituents can be selected from the groups defined as the above-described alkyl groups represented by $R^1$ in formula (1).

The alkoxy groups having 1 to 10 carbon atoms serving as the substituents are preferably linear or branched alkoxy groups having 1 to 5 carbon atoms. Specific examples of the alkoxy groups include a methoxy group, an ethoxy group, a n-propoxy group, an isopropoxy group, a n-butoxy group, an isobutoxy group, a s-butoxy group, a t-butoxy group, a n-pentyloxy group, a n-hexyloxy group, a n-heptyloxy group, a n-octyloxy group, a n-nonyloxy group, a n-decyloxy group, and the like. The alkoxy group is preferably a methoxy group, an ethoxy group, a n-propoxy group, an isopropoxy group, a n-butoxy group, an isobutoxy group, a s-butoxy group, a t-butoxy group, or a n-pentyloxy group.

Examples of the halogen atoms serving as the substituents include chlorine atoms, bromine atoms, fluorine atoms, and the like.

Specific examples of the phenyl group represented by each of $R^2$ and $R^3$ in formula (1) and substituted with the substituents include a 2,4,6-trimethylphenyl group, a 4-methoxyphenyl group, a 2,4,6-trimethoxyphenyl group, a 4-fluorophenyl group, a 2-chlorophenyl group, a 4-chlorophenyl group, a 2,4-dichlorophenyl group, and the like.

The cycloalkyl group having 3 to 8 carbon atoms represented by each of $R^2$ and $R^3$ in formula (1) is preferably a monocyclic, polycyclic, or bridged cycloalkyl group having 5 to 8 carbon atoms, and particularly preferably a monocyclic cycloalkyl group having 5 to 7 carbon atoms. Specific examples of the cycloalkyl group having 3 to 8 carbon atoms include a cyclopropyl group, a cyclobutyl group, a cyclopentyl group, a cyclohexyl group, a cycloheptyl group, a cyclooctyl group, and the like.

The cycloalkyl group represented by each of $R^2$ and $R^3$ in formula (1) optionally has substituents selected from alkyl groups having 1 to 10 carbon atoms. Specific examples of the alkyl groups serving as the substituents include a methyl group, an isopropyl group, a t-butyl group, and the like.

When $R^2$ and $R^3$ in formula (1) form a cycloalkane together with the carbon atoms to which those $R^2$ and $R^3$ are bonded, $R^2$ and $R^3$, taken together, form a preferably 4 to 8-membered and more preferably 5 to 8-membered cycloalkane ring with the adjacent carbon atoms. Preferred examples of the cycloalkane ring include a cyclopentane ring, a cyclohexane ring, and a cycloheptane ring. In the cycloalkane ring, some of the hydrogen atoms may be replaced by alkyl groups having 1 to 10 carbon atoms. Specific examples of the alkyl groups serving as the substituents include a methyl group, an isopropyl group, a t-butyl group, and the like.

Y represents a hydrogen atom or a deuterium atom.

In formula (1), $R^{11}$, $R^{12}$, $R^{13}$, $R^{14}$, $R^{15}$, and $R^{16}$ each independently represent a group selected from a hydrogen atom, alkyl groups having 1 to 10 carbon atoms, silyl groups having 1 to 3 alkyl groups having 1 to 10 carbon atoms, alkoxy groups having 1 to 10 carbon atoms, and —C(=O)—OR$^{22}$, wherein $R^{22}$ represents an alkyl group having 1 to 10 carbon atoms, a heteroaryl group having 4 to 10 carbon atoms, or an aryl group having 6 to 10 carbon atoms. In addition, $R^{11}$, $R^{12}$, $R^{13}$, $R^{14}$, $R^{15}$, and $R^{16}$ in formula (1) are each independently preferably selected from a hydrogen atom and alkyl groups having 1 to 10 carbon atoms, further preferably selected from a hydrogen atom and alkyl groups having 1 to 5 carbon atoms, and especially particularly preferably selected from a hydrogen atom and alkyl groups having 1 to 3 carbon atoms.

The alkyl group having 1 to 10 carbon atoms represented by each of $R^{11}$, $R^{12}$, $R^{13}$, $R^{14}$, $R^{15}$, and $R^{16}$ in formula (1) can be selected from the groups defined as the alkyl groups having 1 to 10 carbon atoms represented by $R^1$, and is desirably selected from a methyl group, an ethyl group, a n-propyl group, and an isopropyl group.

The silyl groups having 1 to 3 alkyl groups having 1 to 10 carbon atoms represented by each of $R^{11}$, $R^{12}$, $R^{13}$, $R^{14}$, $R^{15}$, and $R^{16}$ in formula (1) include silyl groups substituted with 1, 2, or 3 alkyl groups, and is preferably a tri-substituted alkylsilyl group. The alkyl groups can be selected from the groups defined as the alkyl groups having 1 to 10 carbon atoms represented by $R^1$, and specifically may be a methyl group, an ethyl group, a n-propyl group, an isopropyl group, a n-butyl group, an isobutyl group, a s-butyl group, a t-butyl group, a n-pentyl group, a n-hexyl group, a n-heptyl group, a n-octyl group, a n-nonyl group, a n-decyl group, and the like. Specific examples of the silyl group include a trimethylsilyl group, a triethylsilyl group, a t-butyldimethylsilyl group, a triisopropylsilyl group, and the like.

The alkoxy group having 1 to 10 carbon atoms represented by each of $R^{11}$, $R^{12}$, $R^{13}$, $R^{14}$, $R^{15}$, and $R^{16}$ in formula (1) can be selected from the alkoxy groups defined as the substituents of the phenyl group represented by each of $R^2$ and $R^3$ described above.

$R^{22}$ in —C(=O)—$OR^2$ represented by each of $R^{11}$, $R^{12}$, $R^{13}$, $R^{14}$, $R^{15}$, and $R^{16}$ in formula (1) represents an alkyl group having 1 to 10 carbon atoms, a heteroaryl group having 4 to 10 carbon atoms, or an aryl group having 6 to 10 carbon atoms. The alkyl group having 1 to 10 carbon atoms may be any one of linear, branched, and cyclic forms, and is preferably a linear alkyl group having 1 to 6 carbon atoms. The heteroaryl group having 4 to 10 carbon atoms is a heteroaryl group which contains at least one heteroatom and which is of a monocyclic, polycyclic, fused cyclic, or other ring system, and is preferably a monocyclic heteroaryl group containing 1 to 3 heteroatoms and having a 4 to 8-membered ring. The heteroatoms include a nitrogen atom, an oxygen atom, a sulfur atom, and the like. The aryl group having 6 to 10 carbon atoms may be in the form of any one of an aromatic monocyclic group, an aromatic polycyclic group, and an aromatic fused cyclic group, and is preferably an aromatic monocyclic group having 6 to 8 carbon atoms. The alkyl group having 1 to 10 carbon atoms may be a methyl group, an ethyl group, a n-propyl group, a n-butyl group, a t-butyl group, a n-pentyl group, a n-hexyl group, a cyclohexyl group, or the like, and the aryl group having 6 to 10 carbon atoms may be a phenyl group or the like.

$Q^-$ in formula (1) represents a counter anion. Specific counter anions include ions such as $BF_4^-$, $SbF_6^-$, $CF_3COO^-$, $CH_3COO^-$, $PF_6^-$, $NO_3^-$, $ClO_4^-$, $SCN^-$, $OCN^-$, $ReO_4^-$, $MoO_4^-$, $BPh_4^-$, $B(C_6F_5)_4^-$, and $B(3,5-(CF_3)_2C_6F_3)_4^-$. Of these ions, $BF_4^-$ is preferable.

<Ruthenium Complex (Complex Represented by General Formula (2))>

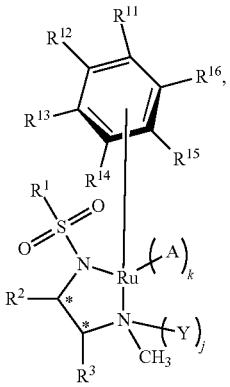

(2)

wherein * indicates an asymmetric carbon atom.

In formula (2), $R^1$, $R^2$, $R^3$, $R^{11}$, $R^{12}$, $R^{13}$, $R^{14}$, $R^{15}$, $R^{16}$, and Y are as defined above.

In formula (2), A represents a group selected from a trifluoromethanesulfonyloxy group, a p-toluenesulfonyloxy group, a methanesulfonyloxy group, a benzenesulfonyloxy group, a hydrogen atom, a deuterium atom, and halogen atoms.

The halogen atoms include a chlorine atom, a bromine atom, an iodine atom, and the like.

In formula (2), j and k each represent 0 or 1, provided that j+k is not 1.

<Iridium or Rhodium Complex (Complex Represented by General Formula (3))>

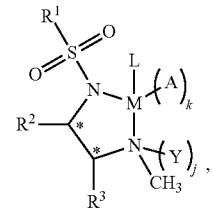

(3)

wherein * indicates an asymmetric carbon atom.

In formula (3), $R^1$, $R^2$, $R^3$, A, and Y are as defined above.

In formula (3), M represents iridium or rhodium.

In formula (3), L represents a Cp (cyclopentadienyl) or Cp* (pentamethylcyclopentadienyl) ligand.

In formula (3), j and k each represent 0 or 1, provided that j+k is not 1.

<Iridium or Rhodium Complex (Complex Represented by General Formula (4))>

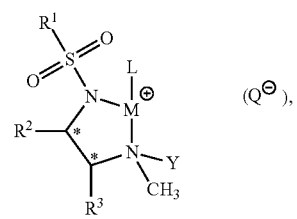

(4)

wherein * indicates an asymmetric carbon atom.

In formula (4), $R^1$, $R^2$, $R^3$, Y, M, L, and $Q^-$ are as defined above.

In addition, the complexes of general formulae (1) to (4) can be produced by, for example, the method shown in schemes 1 to 6 below.

<Methods for Producing Complexes Represented by General Formulae (1) to (4)>

First, methods for producing the ruthenium complexes represented by general formulae (1) and (2) are described on the basis of schemes 1 to 3.

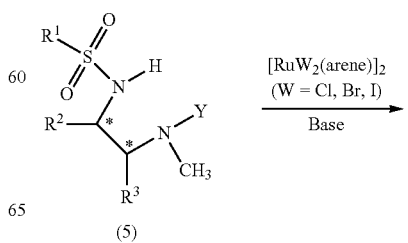

(Scheme 1)

(5)

-continued

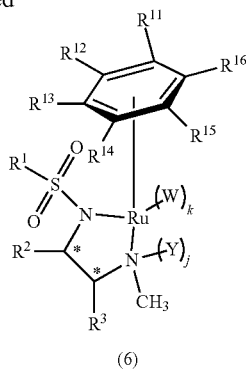

(6)

In scheme 1, *, $R^1$, $R^2$, $R^3$, Y, $R^{11}$, $R^{12}$, $R^{13}$, $R^{14}$, $R^{15}$, $R^{16}$, j, and k are as defined above. W represents a chlorine atom, a bromine atom, or an iodine atom. The method shown in scheme 1 is described in, for example, Angew. Chem. Int. Ed. Engl., 1997, 36, p. 285 and in J. Am. Chem. Soc. 117 (1995), p. 7562. Note that the diamine compound represented by general formula (5) can be obtained by direct methylation of a monosulfonyldiamine or by hydride reduction of a compound methoxycarbonylated by using methyl chloroformate or the like.

Examples of the ruthenium compound ($[RuW_2(arene)]_2$ in Scheme 1) serving as a starting raw material of the complex represented by general formula (6) include $[RuCl_2(p\text{-cymene})]_2$, $[RuI_2(p\text{-cymene})]_2$, $[RuBr_2(p\text{-cymene})]_2$, $[RuBr_2(benzene)]_2$, $[RuI_2(benzene)]2$, $[RuCl_2(benzene)]2$, $[RuBr_2(mesitylene)]_2$, $[RuI_2(mesitylene)]_2$, $[RuCl_2(mesitylene)]_2$, $[RuCl_2(hexamethylbenzene)]_2$, $[RuI_2(hexamethylbenzene)]_2$, $[RuBr_2(hexamethylbenzene)]_2$, $[RuBr_2(toluene)]_2$, $[RuI_2(toluene)]_2$, $[RuCl_2(toluene)]_2$, $[RuBr_2(xylene)]_2$, $[RuI_2(xylene)]_2$, $[RuCl_2(xylene)]_2$, $[RuCl_2$ (TMS-benzene)$]_2$, $[RuCl_2(\text{TMS-toluene})]_2$, and the like.

Note that TMS represents trimethylsilyl.

The reaction between the diamine compound represented by general formula (5) and the ruthenium compound in scheme 1 is theoretically an equimolar reaction. However, the diamine compound is preferably used in an equimolar amount or more to the ruthenium compound from the viewpoint of the catalyst preparation speed.

Next, the base used in scheme 1 is described.

When the complex of general formula (6), in which j and k are 1, is prepared, tertiary organic amines such as trimethylamine, triethylamine, triisopropylamine, and diisopropylethylamine are preferable, and triethylamine is particularly preferable.

When the complex of general formula (6), in which j and k are 0, is synthesized, it is preferable to use an inorganic base such as LiOH, NaOH, KOH, or $K_2CO_3$; or a metal alkoxide such as sodium methoxide or potassium methoxide. Of these bases, it is particularly preferable to use a strong base such as NaOH or KOH.

The amount of each base added is preferably equimolar or more to the ruthenium atoms.

Solvents used in scheme 1 include, but are not particularly limited to, ethers such as diethyl ether and tetrahydrofuran; alcohols such as methanol, ethanol, and isopropanol; aromatic hydrocarbons such as toluene and xylene; aprotic polar solvents such as acetonitrile and N,N-dimethylformamide; halogen-containing solvents such as dichloromethane and chloroform; and the like. Of these solvents, isopropanol and dichloromethane are preferable.

The complex of general formula (6) obtained in scheme 1 is equivalent to the ruthenium complex of the present invention represented by general formula (2), in which j and k are 0, or in which j and k are 1 and A is a halogen atom, and falls within the ruthenium complex of the present invention. The complex of general formula (6) serves as a precursor of the ruthenium complex represented by general formula (1), or the ruthenium complex represented by general formula (2), in which j and k are 1 and A is other than halogen atoms.

(Scheme 2)

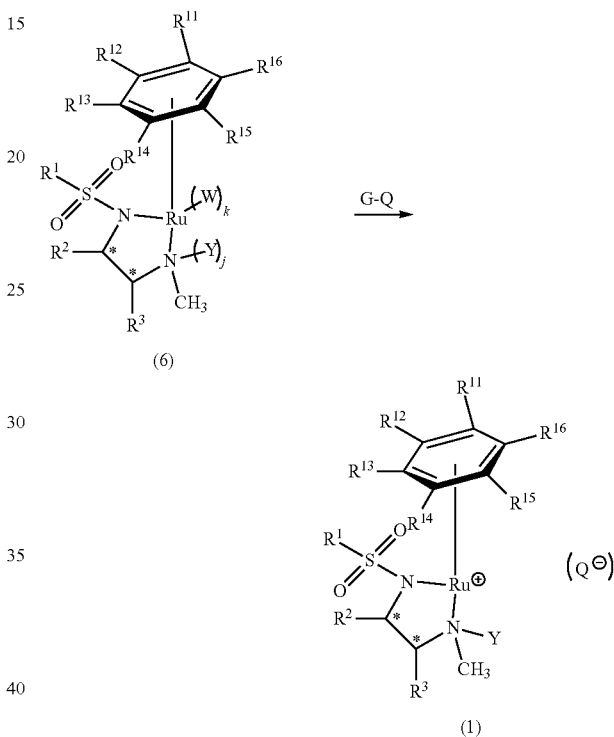

In scheme 2, *, $R^1$, $R^2$, $R^3$, Y, W, $Q^-$, $R^{11}$, $R^{12}$, $R^{13}$, $R^{14}$, $R^{15}$, $R^{16}$, j, and k are as defined above. As shown in scheme 2, the cationic ruthenium complex represented by general formula (1) can be obtained by reacting the ruthenium complex represented by general formula (6), in which j and k are 1, serving as a precursor with a metal salt represented by G-Q.

Examples of the metal G in G-Q in scheme 2 include silver (Ag), sodium (Na), potassium (K), lithium (Li), and the like. Q may be alkanesulfonyloxy or arenesulfonyloxy such as trifluoromethanesulfonyloxy (TfO), p-toluenesulfonyloxy (TsO), methanesulfonyloxy (MsO), or benzenesulfonyloxy (BsO), and further may be $BF_4$, $SbF_6$, $CF_3COO$, $CH_2COO$, $PF_6$, $NO_3$, $ClO_4$, SCN, OCN, $ReO_4$, $MoO_4$, $BPh_4$, $B(C_6F_5)_4$, $B(3,5\text{-}(CF_3)_2C_6F_3)_4$, or the like.

Examples of the metal salt represented by G-Q include AgOTf, AgOTs, AgOMs, AgOBs, $AgBF_4$, $AgSbF_6$, $CF_3COOAg$, $CH_3COOAg$, $AgPF_6$, $AgNO_3$, $AgClO_4$, AgSCN, AgOCN, $AgReO_4$, $AgMoO_4$, NaOTf, $NaBF_4$, $NaSbF_6$, $CF_3COONa$, $CH_3COONa$, $NaPF_6$, $NaNO_3$, $NaClO_4$, NaSCN, KOTf, $KBF_4$, $KSbF_6$, $CF_3COOK$, $CH_3COOK$, $KPF_6$, $KNO_3$, $KClO_4$, KSCN, $KBPh_4$, $KB(C_6F_5)_4$, $KB(3,5\text{-}(CF_3)_2C_6F_3)_4$, LiOTf, $LiBF_4$, $LiSbF_6$, CF₃COOLi, CH₃COOLi, LiPF₆, LiNO₃, LiClO₄, LiSCN, LiBPh₄, LiB(C₆F₅)₄, LiB(3,5-(CF₃)₂C₆F₃)₄, and the like.

The amount of the metal salt G-Q used in scheme 2 is equimolar or more to the ruthenium atoms.

In addition, solvents used in scheme 2 include, but are not particularly limited to, alcohols such as methanol, ethanol, and isopropanol, aromatic hydrocarbons such as toluene and xylene, halogenated hydrocarbons such as dichloromethane and 1,2-dichloroethane, aprotic polar solvents such as acetonitrile and N,N-dimethylformamide, ethers such as diethyl ether and tetrahydrofuran, and the like. Of these solvents, methanol or dichloromethane is preferable. One of the solvents may be used, or a mixture of multiple solvents may be used.

(Scheme 3)

The ruthenium complex represented by general formula (2), in which j and k are 1, and A is a trifluoromethanesulfonyloxy group, a p-toluenesulfonyloxy group, a methanesulfonyloxy group, or a benzenesulfonyloxy group, can be produced by the method shown in scheme 3.

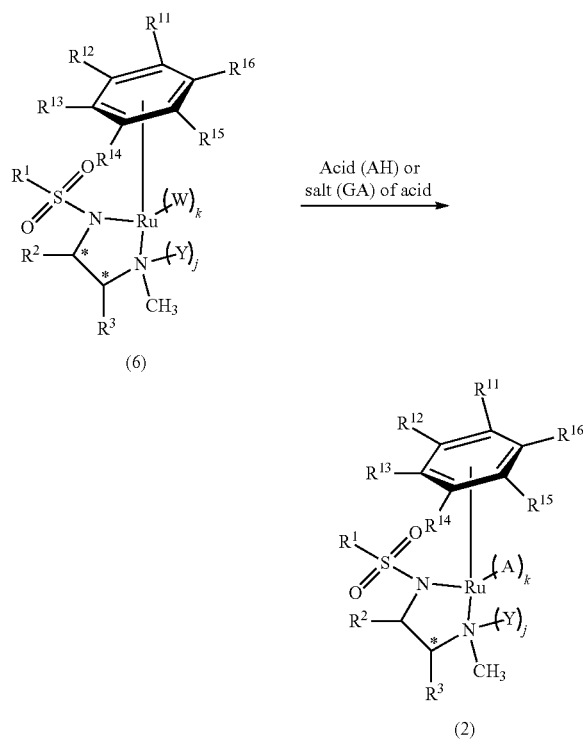

In scheme 3, *, $R^1$, $R^2$, $R^3$, Y, W, $R^{11}$, $R^{12}$, $R^{13}$, $R^{14}$, $R^{15}$, $R^{16}$, j, and k are as defined above.

As shown in scheme 3, the complex of general formula (2) can be produced by adding a suitable salt (GA) of an acid to the complex of general formula (6), in which j and k are 1. Alternatively, the complex of general formula (2) can be produced by adding a suitable acid (AH) to the complex of general formula (6), in which j and k are 0.

G in the salt (GA) of an acid has the same meaning as that of metal G described in scheme 2.

A in GA is a trifluoromethanesulfonyloxy (TfO) group, a p-toluenesulfonyloxy (TsO) group, a methanesulfonyloxy (MsO) group, or a benzenesulfonyloxy (BsO) group.

A in the acid (AH) is a trifluoromethanesulfonyloxy (TfO) group, a p-toluenesulfonyloxy (TsO) group, a methanesulfonyloxy (MsO) group, or a benzenesulfonyloxy (BsO) group.

Solvents usable in scheme 3 are the same as those usable in scheme 2.

Next, methods for producing the complexes represented by general formulae (3) and (4) are described on the basis of scheme 4 to 6.

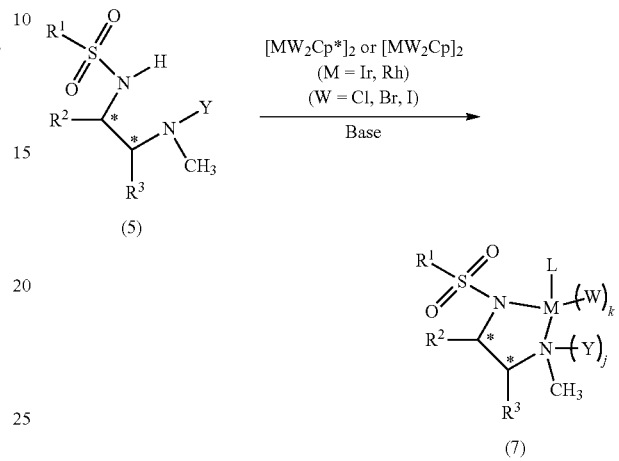

In scheme 4, *, $R^1$, $R^2$, $R^3$, Y, M, L, j, and k are as defined above. W represents a chlorine atom, a bromine atom, or an iodine atom. The method shown in scheme 4 is described in Angew. Chem. Int. Ed. Engl., 1997, 36, p. 285 and in J. Am. Chem. Soc. 117 (1995), p. 7562. Note that the diamine compound represented by general formula (5) can be obtained by direct methylation of a monosulfonyldiamine or by hydride reduction of a compound methoxycarbonylated by using methyl chloroformate or the like.

Examples of the iridium or rhodium compound ([MW₂Cp*]₂ or [MW₂Cp]₂ in Scheme 4) serving as a starting raw material of the complex represented by general formula (7) include [IrCp*Cl₂]₂, [IrCpCl₂]₂, [RhCp*Cl₂]₂, [RhCpCl₂]₂, [IrCp*Br₂]₂, [IrCpBr₂]₂, [RhCp*Br₂]₂, [RhCpBr₂]₂, [IrCp*I₂]₂, [IrCpI₂]₂, [RhCp*I₂]₂, [RhCpI₂]₂, and the like.

The reaction of the diamine compound represented by general formula (5) with the iridium or rhodium compound in scheme 4 is theoretically an equimolar reaction. However, the diamine compound is preferably used in an equimolar amount or more to the iridium or rhodium compound from the viewpoint of the catalyst preparation speed.

Next, the base used in scheme 4 is described.

When the complex of general formula (7), in which j and k are 1, is prepared, a tertiary organic amine such as trimethylamine, triethylamine, triisopropylamine, or diisopropylethylamine is preferable, and triethylamine is particularly preferable.

When the complex of general formula (7), in which j and k are 0, is synthesized, it is preferable to use an inorganic base such as LiOH, NaOH, KOH, or K₂CO₃; or a metal alkoxide such as sodium methoxide or potassium methoxide. Of these bases, it is particularly preferable to use a strong base such as NaOH or KOH.

The amount of each base added is preferably equimolar or more to the ruthenium atoms, iridium atoms, or rhodium atoms.

Solvents used in scheme 4 include, but are not particularly limited to, ethers such as diethyl ether and tetrahydrofuran; alcohols such as methanol, ethanol, and isopropanol; aromatic hydrocarbons such as toluene and xylene; aprotic polar solvents such as acetonitrile and N,N-dimethylformamide; halogen-containing solvents such as dichloromethane and chloroform; and the like. Of these solvents, isopropanol or dichloromethane is preferable.

The complex of general formula (7) obtained in scheme 4 is equivalent to the rhodium or iridium complex of the present invention represented by general formula (3), in which j and k are 0, or in which j and k are 1 and A is a halogen atom, and falls within the rhodium or iridium complex of the present invention. The complex of general formula (7) serves as a precursor of the rhodium or iridium complex represented by general formula (4), or the rhodium or iridium complex represented by general formula (3), in which j and k are 1 and A is other than halogen atoms.

(Scheme 5)

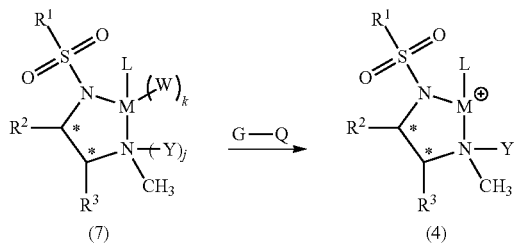

In scheme 5, *, $R^1$, $R^2$, $R^3$, Y, W, $Q^-$, M, L, j, and k are as defined above. The cationic iridium or rhodium complex represented by general formula (4) can be obtained by reacting the iridium or rhodium complex represented by general formula (7), in which j and k are 1, with a metal salt represented by G-Q.

G-Q in scheme 5 is as defined in scheme 2.

The amount of the metal salt G-Q used in scheme 5 is equimolar or more to the iridium atoms or the rhodium atoms.

In addition, solvents usable in scheme 5 are the same as those usable in scheme 2.

(Scheme 6)

The iridium or rhodium complex represented by general formula (3), in which j and k are 1, and A is a trifluoromethanesulfonyloxy group, a p-toluenesulfonyloxy group, a methanesulfonyloxy group, or a benzenesulfonyloxy group, can be produced by the method shown in scheme 6.

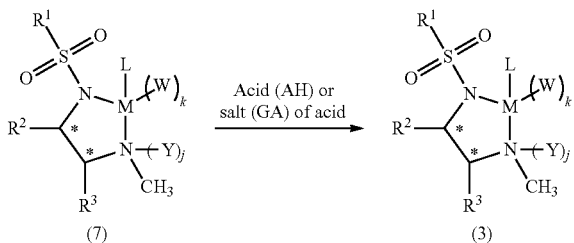

In scheme 6, *, $R^1$, $R^2$, $R^3$, Y, W, M, L, j, and k are as defined above.

As shown in scheme 6, the complex of general formula (3) can be produced by adding a suitable salt (GA) of an acid to the complex of general formula (7), in which j and k are 1. Alternatively, the complex of general formula (3) can be produced by adding a suitable acid (AH) to the complex of general formula (7), in which j and k are 0.

G in the salt (GA) of an acid has the same meaning as that of the metal G described in scheme 2.

A in GA and A in the acid (AH) are as defined in scheme 3.

Solvents usable in scheme 6 are the same as those usable in scheme 5.

After completion of the preparation reaction of the complex, the target ruthenium complex, iridium complex, or rhodium complex can be separated by a usual crystallization technique such as concentration of the reaction liquid or addition of a poor solvent.

In addition, when a hydrogen halide salt is by-produced during the preparation of the complex, a washing operation with water may be conducted, if necessary.

The thus obtained complex represented by general formula (1), (2), (3), or (4) of the present invention can be used as a catalyst for an asymmetric reduction reaction of the present invention.

Note that the asymmetric reduction reaction may be carried out by using the ruthenium complex represented by general formula (1) or (2) or the iridium or rhodium complex represented by general formula (3) or (4) of the present invention after isolation. Alternatively, the reaction may be carried out without isolation of the complex by directly using the reaction liquid in which the complex is prepared (in-situ method).

In addition, each of the ruthenium complex represented by general formula (2) and the iridium or rhodium complex represented by general formula (3), in which A is other than a hydrogen atom, can be easily converted to a complex of the corresponding general formula, in which A is a hydrogen atom, by being brought into contact with hydrogen gas.

The amount used only needs to be equimolar amount or more, in terms of hydride, to the complex of general formula (2) or general formula (3).

In addition, the replacement of A in the complex of the present invention with a hydrogen atom may be conducted in advance before being used in an asymmetric reduction reaction, or may be conducted in an asymmetric reduction reaction system.

<Method for Producing Optically Active Compound>

A method for producing an optically active compound of the present invention comprises the step of reducing an imino group of an imine compound or reducing an unsaturated bond in a ring of a heterocyclic compound by using the above-described ruthenium complex, iridium complex, or rhodium complex as a catalyst in the presence of hydrogen gas serving as a hydrogen donor.

The reduction reaction of the imine compound or the heterocyclic compound in the production method of the present invention is an asymmetric reduction reaction, and, specifically, is an asymmetric hydrogenation reaction using hydrogen gas as a hydrogen donor. In addition, the use of hydrogen gas as the hydrogen donor makes it possible to achieve an unexpectedly high reduction efficiency and an unexpectedly high optical purity of the imine compound or the heterocyclic compound.

The imine compound is not particularly limited, as long as the compound has an imino group.

Examples of the heterocyclic compound include heterocyclic compounds containing one or more heteroatoms selected from nitrogen atoms, oxygen atoms, sulfur atoms, and the like. Of these heterocyclic compounds, an unsaturated bond in a ring of a heterocyclic compound containing at least one nitrogen atom as a heteroatom is preferably reduced to produce the optically active amine.

Specific optically active compounds in the present invention include optically active amines each obtained by reducing an imino group of an imine compound; optically active amines each obtained by reducing a quinoline derivative, a quinoxaline derivative, an indole derivative, or the like; and the like.

In the asymmetric reduction reaction, a base may further be used. The base may be a tertiary organic amine such as trimethylamine, triethylamine, or triisopropylamine; an inorganic base such as LiOH, NaOH, KOH, or $K_2CO_3$; or a metal alkoxide such as sodium methoxide or potassium methoxide.

Reaction solvents used in the reaction using hydrogen gas as the hydrogen donor include alcohols such as methanol, ethanol, 2-propanol, tert-butyl alcohol, trifluoroethanol, and hexafluoroisopropanol, aprotic solvents such as toluene, tetrahydrofuran, 2-methyltetrahydrofuran, acetonitrile, and acetone, halogen-containing solvents such as dichloromethane and chloroform, and the like.

The amount of each of the complexes represented by general formulae (1) to (4) used as a catalyst is selected such that the mole ratio (S/C) of the substrate (i.e., the imine compound or the heterocyclic compound) (S) to the ruthenium, iridium, or rhodium metal atoms (C) can be in the range from 10 to 1000000, and preferably from 50 to 15000.

The reaction temperature is selected in the range from −20 to 100° C., and preferably from 0 to 70° C.

The reaction pressure of hydrogen gas is generally 10 MPa or lower, and preferably 0.1 to 5 MPa.

The reaction time is 1 to 100 hours, and generally 2 to 50 hours, although it varies depending on the catalyst ratio.

After the reaction, the formed optically active compound can be separated and purified by usual operations such as distillation, extraction, chromatography, and recrystallization.

Hereinafter, the present invention will be described in detail based on Examples; however, the present invention is not limited thereto.

EXAMPLES

In the following Examples etc., NMR spectra used to identify the complexes and determine the purities of the complexes were acquired on Mercury Plus 300 4N model spectrometer manufactured by Varian Technologies Japan, Ltd., or on Bruker BioSpin Avance III 500 System. For the GC analyses, Chirasil-DEXCB (0.25 mm×25 m, 0.25 μm) (manufactured by Varian, Inc.) or HP-1 (0.32 mm×30 m, 0.25 μm) (manufactured by Agilent Technologies, Inc.) was used. For the HPLC analysis, YMC-Pack Pro C18 (250×4.6 mm, 5 μm, 12 nm) (manufactured by YMC) and CHIRALCEL OD-H (250×4.6 mm) (manufactured by DAICEL) were used. In addition, for the MS measurement, JMS-T100GCV manufactured by JEOL Ltd. or LCMS-IT-TOF manufactured by Shimadzu Corporation was used.

In addition, symbols in Examples have the following meanings.

HFIP: hexafluoroisopropanol
Ts: tosyl
Ph: phenyl
Me: methyl
p-cymene: p-isopropyltoluene
Tipps: 2,4,6-triisopropylbenzenesulfonyl
DPEN: 1,2-diphenylethylenediamine
Ms: mesyl
$RuBF_4$ ((R,R)-Tsdpen) (p-cymene):

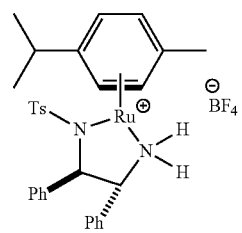

RuOTf ((R,R)-Tsdpen) (p-cymene):

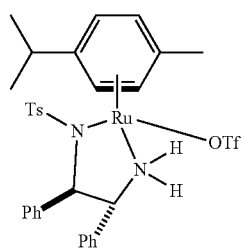

Cp*IrBF$_4$ ((R,R)-Tsdpen):

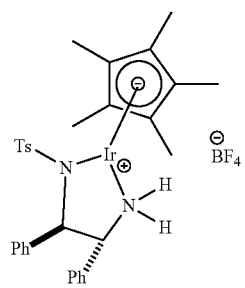

Synthesis Example 1

Synthesis of (1R,2R)—N-Me-TsDPEN (Compound 3) (synthesis of diamine compound usable for synthesis of complexes of general formulae (1) to (4))

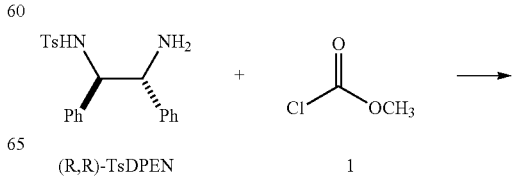

-continued

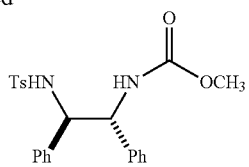

2

A three-way stopcock, a stir bar, a dropping funnel, and a thermometer were attached to a 500 mL 4-necked reaction flask, and the inside of the reaction flask was purged with nitrogen. To this reaction flask, 5.0 g (13.64 mmol) of (R,R)-TsDPEN, 2.578 g (2.11 mL, 27.28 mmol) of methyl chloroformate (Compound 1), 5.652 g (40.93 mmol) of potassium carbonate, 27.3 mL of water, and 27.3 mL of tetrahydrofuran (hereinafter, referred to as THF) were added under a nitrogen stream, followed by stirring at room temperature for 1 hour. The conversion was checked by TLC, and the raw material had disappeared. At this time point, the reaction was terminated, and 82 mL of toluene and 27 mL of water were added. After stirring, the mixture was allowed to stand, and then the aqueous layer was removed. The obtained organic layer was directly concentrated to dryness by removing the solvent using an evaporator. Thus, 6.28 g of an almost pure compound, 2(N-((1R,2R)-2-(4-methylphenylsulfonamide)-1,2-diphenylethyl) acetamide), was obtained. This compound was used in the subsequent reaction without further purification.

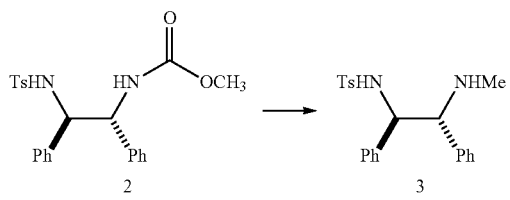

To the entire amount of the obtained Compound 2, 273 mL of toluene and 11.8 g (10.6 mL, 40.9 mmol) of Vitride (registered trademark) (70% toluene solution), which was a reducing agent, were added, and the reaction was allowed to proceed in an oil bath at 120° C. under reflux for 1 hour. The conversion was checked by TLC, and the raw material had disappeared. At this time point, the reaction was terminated, and 10 mL of water was slowly added to the reaction liquid under ice-cooling. After that, 80 mL of water was further added, and the mixture was stirred, and allowed to stand. Then, the aqueous layer was separated. After this washing operation was repeated twice, the solvent in the organic layer was recovered using an evaporator, and the obtained concentrate was purified by silica gel column chromatography. Thus, 3.66 g of Compound 3 (diamine compound) was obtained (Yield: 70.5%).

$^1$H-NMR (CDCl$_3$, 300 MHz): δ 7.41-7.37 (d, 2H), 7.20-7.15 (m, 3H), 7.15-7.00 (m, 5H), 7.00-6.92 (m, 4H), 4.30 (d, 1H), 3.57 (d, 1H), 2.33 (s, 3H), 2.21 (s, 3H);

HRMS (ESI) calcd for C$_{22}$H$_{25}$N$_2$O$_2$S [M+H]+ 381.1637, found 381.1627.

Synthesis Example 2

Synthesis of Ruthenium Complex (RuCl((R,R)—N-Me-Tsdpen) (p-cymene)) (ruthenium complex of general formula (2))

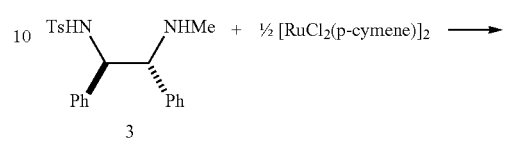

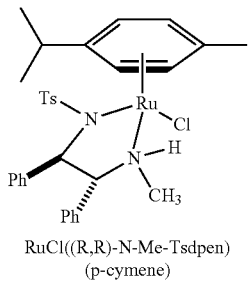

RuCl((R,R)-N-Me-Tsdpen) (p-cymene)

Compound 3 (1.0 g, 2.628 mmol) obtained in Synthesis Example 1, [RuCl$_2$(p-cymene)]$_2$ (0.804 g, 2.628 mmol (in terms of Ru)), and 0.531 g (0.74 mL, 5.256 mmol) of triethylamine were dissolved in 20 mL of 2-propanol, and the reaction was allowed to proceed at 70° C. for 1 hour. After that, the solvent was recovered from the reaction liquid, and 10 mL of water was added, followed by stirring for 10 minutes under ice-cooling. The precipitated crystals were filtered, and then dried under reduced pressure. Thus, 1.5 g of RuCl((R,R)—N-Me-Tsdpen) (p-cymene) was obtained (Yield: 86.8%).

$^1$H-NMR (CD$_2$Cl$_2$, 300 MHz): δ 7.15-7.05 (m, 6H), 6.82-6.75 (m, 4H), 6.70-6.62 (m, 2H), 6.60-6.55 (m, 2H), 5.75 (d, 1H), 5.50 (d, 1H), 5.43-5.40 (m, 2H), 4.02 (d, 1H), 4.00 (brs, 1H), 3.45 (t, 1H), 3.25-3.15 (m, 1H), 2.80 (d, 1H), 2.42 (s, 3H), 2.22 (s, 3H), 1.40 (d, 6H);

HRMS (ESI) calcd for C$_{32}$H$_{37}$N$_2$O$_2$RuS [M-Cl]+ 615.1619, found 615.1613.

Synthesis Example 3

Synthesis of Ruthenium Complex (RuBF$_4$((R,R)—N-Me-Tsdpen) (p-cymene)) (ruthenium complex of general formula (1))

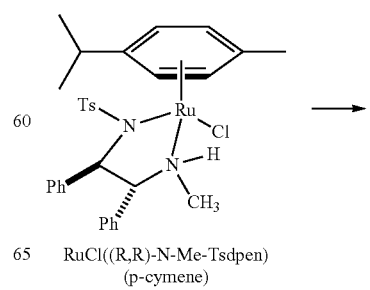

RuCl((R,R)-N-Me-Tsdpen) (p-cymene)

-continued

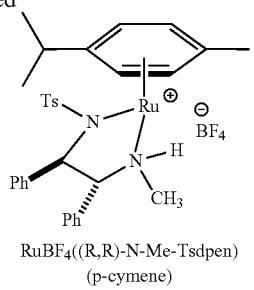

RuBF$_4$((R,R)-N-Me-Tsdpen)
(p-cymene)

In 10 mL of methanol and 10 mL of dichloromethane, 1.0 g (1.54 mmol) of the ruthenium complex, RuCl((R,R)—N-Me-Tsdpen) (p-cymene), obtained in Synthesis Example 2 and 0.359 g (1.846 mmol) of AgBF$_4$ were stirred for 1 hour. After the precipitated salt was filtered through Celite, the filtrate was concentrated using an evaporator and dried under reduced pressure. Thus, 1.05 g of RuBF$_4$((R,R)—N-Me-Tsdpen) (p-cymene), which is a ruthenium complex of the present invention, was obtained (Yield: 99%).

$^1$H-NMR (CD$_3$OD, 300 MHz): δ 7.22-6.58 (m, 14H), 6.13 (d, 1H), 6.00-5.92 (m, 2H), 5.82 (d, 1H), 4.15 (d, 1H), 4.00-3.85 (brs, 1H), 3.70 (t, 1H), 3.02 (d, 1H), 2.18 (s, 3H), 2.20 (s, 3H), 1.48-1.38 (m, 6H);

HRMS (ESI) calcd for C$_{32}$H$_{37}$N$_2$O$_2$RuS [M-BF$_4$]$^+$ 615.1619, found 615.1607.

Synthesis Example 4

Synthesis of Ruthenium Complex (RuOTf((R,R)—N-Me-Tsdpen) (p-cymene)) (ruthenium complex of general formula (2))

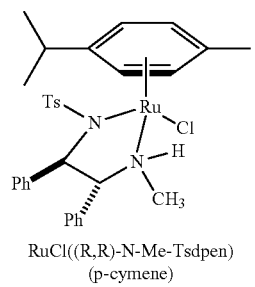

RuCl((R,R)-N-Me-Tsdpen)
(p-cymene)

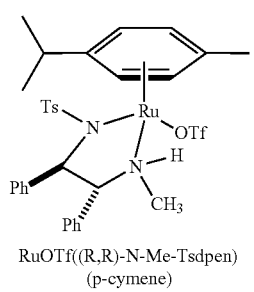

RuOTf((R,R)-N-Me-Tsdpen)
(p-cymene)

In 5 mL of methanol and 5 mL of dichloromethane, the ruthenium complex, 0.5 g (0.769 mmol) of RuCl((R,R)—N-Me-Tsdpen) (p-cymene) obtained in Synthesis Example 2 and 0.237 g (0.922 mmol) of AgOTf were stirred for 1 hour. After the precipitated salt was filtered through Celite, the filtrate was concentrated using an evaporator and dried under reduced pressure. Thus, 0.58 g of RuOTf((R,R)—N-Me-Tsdpen) (p-cymene), which is a ruthenium complex of the present invention, was obtained (Yield: 99%).

$^1$H-NMR (CD$_3$OD, 300 MHz): δ 7.22-6.58 (m, 14H), 6.13 (d, 1H), 6.00-5.92 (m, 2H), 5.82 (d, 1H), 4.15 (d, 1H), 4.00-3.85 (brs, 1H), 3.70 (t, 1H), 3.02 (d, 1H), 2.18 (s, 3H), 2.20 (s, 3H), 1.48-1.38 (m, 6H);

HRMS (ESI) calcd for C$_{32}$H$_{37}$N$_2$O$_2$RuS [M-OTf]$^+$ 615.1619, found 615.1611.

Synthesis Example 5

Synthesis of (1S,2S)—N-Me-TippsDPEN (Compound 5) (synthesis of diamine compound usable for synthesis of complexes of general formulae (1) to (4))

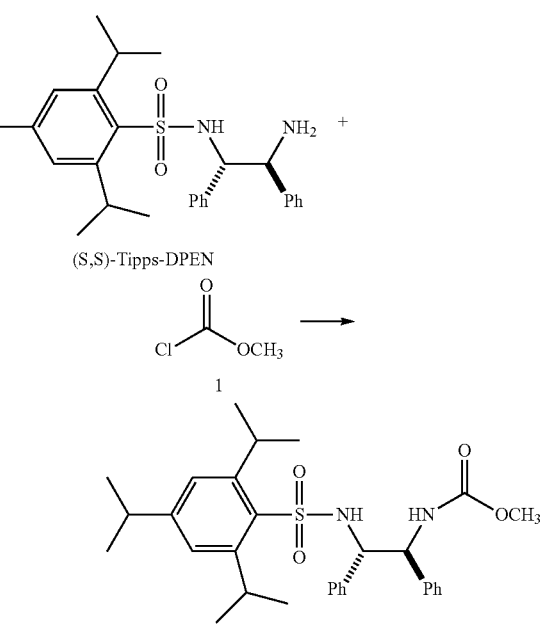

A three-way stopcock, a stir bar, a dropping funnel, and a thermometer were attached to a 500 mL 4-necked reaction flask, and the inside of the flask was purged with nitrogen. To this reaction flask, 5.0 g (10.44 mmol) of (S,S)-Tipps-DPEN, 1.974 g (1.61 mL, 20.9 mmol) of methyl chloroformate (Compound 1), 4.327 g (31.3 mmol) of potassium carbonate, 21 mL of water, and 27.33 mL of THF were added under a nitrogen stream, followed by stirring at room temperature for 1 hour. The conversion was checked by TLC, and the raw material had been disappeared. At this time point, the reaction was terminated, and 61 mL of toluene and 21 mL of water were added, followed by stirring. Then, after the mixture was allowed to stand, the aqueous layer was removed. The obtained organic layer was directly concentrated to dryness by removing the solvent using an evaporator. Thus, 6.0 g of almost pure Compound 4, (N-((1S,2S)-1,2-diphenyl-2-(2,4,6-triisopropylphenylsulfonamide)ethyl)acetamide), was obtained. This compound was used in the subsequent reaction without further purification.

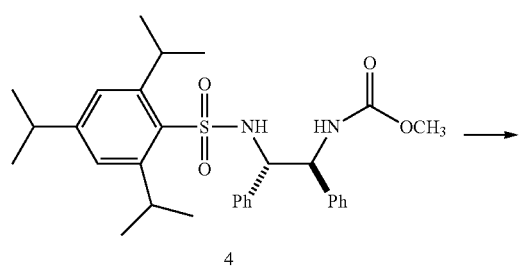

4

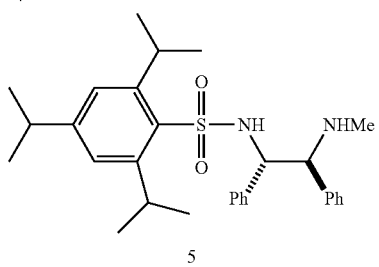

5

To the entire amount of the obtained Compound 4, 209 mL of toluene and 9.05 g (8.07 mL, 31.3 mmol) of Vitride (registered trademark), which was a reducing agent, were added, and the reaction was allowed to proceed in an oil bath at 120° C. under reflux for 1 hour. The conversion was checked by TLC, and the raw material had disappeared. At this time point, the reaction was terminated, and 10 mL of water was slowly added to the reaction liquid under ice-cooling. After that, 70 mL of water was further added, followed by stirring. Then, after the mixture was allowed to stand, the aqueous layer was separated. After this washing operation was repeated twice, the solvent in the organic layer was recovered using an evaporator, and the obtained concentrate was purified by silica gel column chromatography. Thus, 4.65 g of Compound 5 (diamine compound) was obtained (Yield: 90.4%).

$^1$H-NMR (CDCl$_3$, 300 MHz): δ 7.20-7.15 (m, 3H), 7.00-6.85 (m, 7H), 6.78-6.75 (m, 2H), 4.43 (d, 1H), 4.05-3.95 (m, 2H), 3.50 (d, 1H), 2.85-2.80 (m, 1H), 2.27 (s, 3H), 1.25-1.10 (m, 12H), 1.12-1.08 (s, 6H);

HRMS (ESI) calcd for C$_{30}$H$_{41}$N$_2$O$_2$S [M+H]; 493.2889, found 493.2876.

Synthesis Example 6

Synthesis of Ruthenium Complex (RuCl((S,S)—N-Me-Tippsdpen) (benzene)) (ruthenium complex of general formula (2))

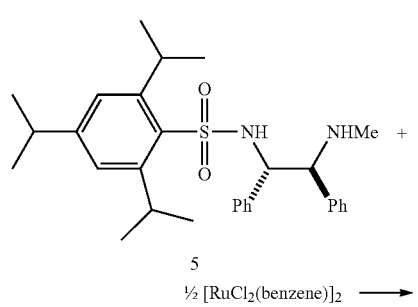

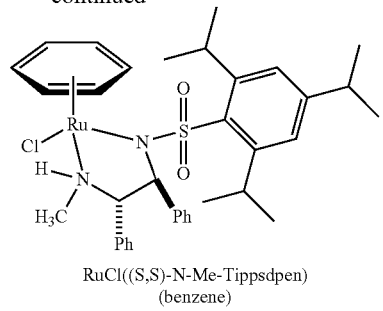

RuCl((S,S)-N-Me-Tippsdpen) (benzene)

Compound 5 (0.5 g, 1.015 mmol) obtained in Synthesis Example 5, [RuCl$_2$(benzene)]z (0.254 g, 1.015 mmol (in terms of Ru)), and 0.205 g (0.29 mL, 2.03 mmol) of triethylamine were dissolved in 10 mL of 2-propanol, and the reaction was allowed to proceed at 80° C. for 1 hour. After that, the solvent was recovered from the reaction liquid, and 10 mL of water was added, followed by stirring for 10 minutes under ice-cooling. The precipitated crystals were filtered, and then dried under reduced pressure. Thus, 0.61 g of RuCl((S,S)—N-Me-Tippsdpen) (benzene) was obtained (Yield: 85.2%).

$^1$H-NMR (CD$_2$Cl$_2$, 300 MHz): δ 7.20-6.50 (m, 12H), 5.90-5.80 (m, 6H), 4.35-4.20 (m, 2H), 4.15 (d, 1H), 3.60 (t, 1H), 2.90 (d, 3H), 2.70-2.60 (m, 1H), 1.30-1.02 (m, 18H);

HRMS (ESI) calcd for C$_{36}$H$_{45}$N$_2$O$_2$RuS [M-Cl]$^+$ 671.2245, found 671.2239.

Synthesis Example 7

Synthesis of Ruthenium Complex (RuBF$_4$((S,S)—N-Me-Tippsdpen) (benzene)) (ruthenium complex of general formula (1))

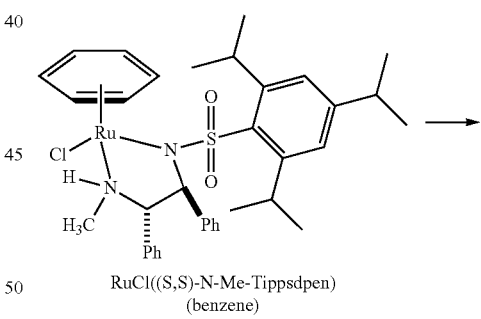

RuCl((S,S)-N-Me-Tippsdpen) (benzene)

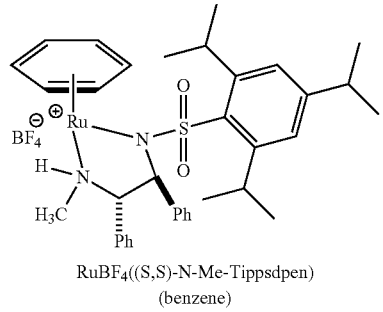

RuBF$_4$((S,S)-N-Me-Tippsdpen) (benzene)

In 7 mL of methanol and 7 mL of dichloromethane, 0.656 g (0.928 mmol) of the ruthenium complex, RuCl((S,S)—N-Me-Tippsdpen) (benzene), obtained in Synthesis Example 6 and 0.216 g (1.11 mmol) of AgBF$_4$ were stirred for 1 hour. After the precipitated salt was filtered through Celite, the filtrate was concentrated using an evaporator and dried under reduced pressure. Thus, 0.68 g of RuBF$_4$((S,S)—N-Me-Tippsdpen) (benzene), which is a ruthenium complex of the present invention, was obtained (Yield: 99%).

$^1$H-NMR (CD$_2$Cl$_2$, 300 MHz): δ 7.22-6.55 (m, 12H), 6.10-6.05 (s, 6H), 4.48 (d, 1H), 4.25-4.15 (m, 2H), 4.00 (t, 1H), 3.10 (d, 3H), 2.70-2.60 (m, 1H), 1.25-1.05 (m, 18H);

HRMS (ESI) calcd for C$_{36}$H$_{45}$N$_2$O$_2$RuS [M-BF$_4$]$^+$ 671.2245, found 671.2238.

Synthesis Example 8

Synthesis of Ruthenium Complex (RuCl((S,S)—N-Me-Tippsdpen) (p-cymene)) (ruthenium complex of general formula (2))

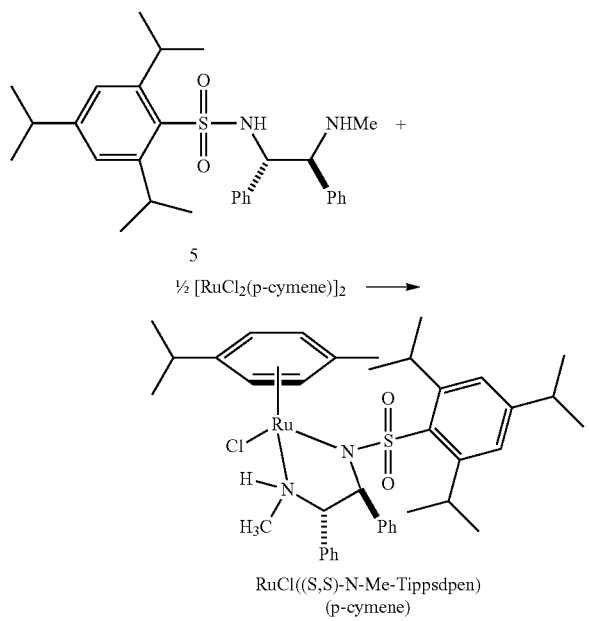

In 20 mL of 2-propanol, 1.0 g (2.03 mmol) of Compound 5 obtained in Synthesis Example 5, 0.62 g (2.03 mmol (in terms of Ru)) of [RuCl$_2$(p-cymene)]$_2$, and 0.41 g (0.574 mL, 4.06 mmol) of triethylamine were dissolved, and the reaction was allowed to proceed at 80° C. for 1 hour. After that, the solvent was recovered from the reaction liquid, and 10 mL of water was added, followed by stirring for 10 minutes under ice-cooling. The precipitated crystals were filtered, and then dried under reduced pressure. Thus, 1.31 g of RuCl((S,S)—N-Me-Tippsdpen) (p-cymene) was obtained (Yield: 85.0%).

$^1$H-NMR (CD$_3$OD, 300 MHz): δ 7.10-6.40 (m, 12H), 5.85-5.65 (m, 4H), 4.25 (d, 1H), 4.18-4.00 (m, 2H), 3.80 (t, 1H), 3.18-3.02 (m, 1H), 2.75 (s, 3H), 2.68-2.60 (m, 1H), 2.42 (s, 3H), 1.50-0.95 (m, 24H);

HRMS (ESI) calcd for C$_{40}$H$_{53}$N$_2$O2RuS [M-Cl]$^+$ 727.2871, found 659.1672.

Synthesis Example 9

Synthesis of Ruthenium Complex (RuBF$_4$((S,S)—N-Me-Tippsdpen) (p-cymene)) (ruthenium complex of general formula (1))

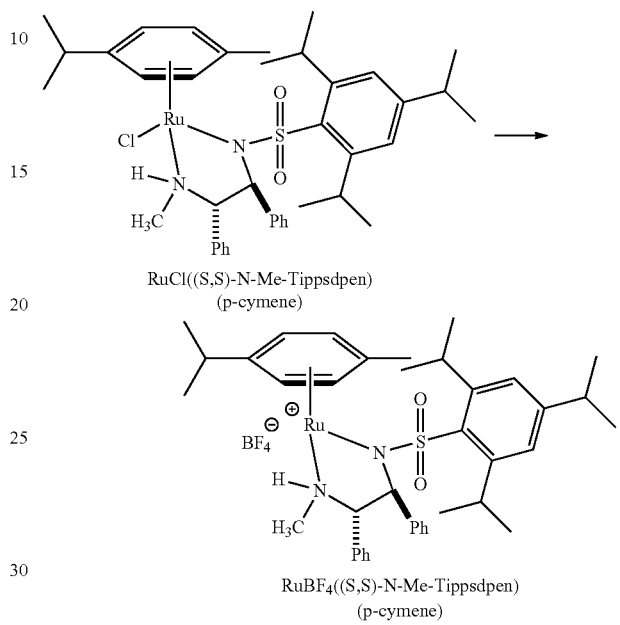

In 6 mL of methanol and 67 mL of dichloromethane, 0.50 g (0.655 mmol) of the ruthenium complex, RuCl((S,S)—N-Me-Tippsdpen) (p-cymene), obtained in Synthesis Example 8 and 0.153 g (0.787 mmol) of AgBF$_4$ were stirred for 1 hour. After the precipitated salt was filtered through Celite, the filtrate was concentrated using an evaporator and dried under reduced pressure. Thus, 0.53 g of RuBF$_4$((S,S)—N-Me-Tippsdpen) (p-cymene), which is a ruthenium complex of the present invention, was obtained (Yield: 99%).

$^1$H-NMR (CD$_3$OD, 300 MHz): δ 7.30-6.82 (m, 12H), 6.00-5.20 (m, 4H), 4.58 (d, 1H), 4.30-4.18 (m, 2H), 4.10 (t, 1H), 3.10 (s, 3H), 3.00-2.80 (m, 2H), 2.25 (s, 3H), 1.48-0.85 (m, 24H);

HRMS (ESI) calcd for C$_{40}$H$_{53}$N$_2$O$_2$RuS [M-BF$_4$]$^+$ 727.2871, found 727.2859.

Example 1

Hydrogenation Reaction of 2-Methylquinoline using RuBF$_4$((R,R)—N-Me-Tsdpen) (p-cymene) (asymmetric reduction reaction of the present invention)

A 100 mL autoclave was charged with 3.5 mg (0.005 mmol, S/C=500) of RuBF$_4$((R,R)—N-Me-Tsdpen) (p-cymene) obtained in Synthesis Example 3 serving as a catalyst, 0.358 g (0.34 mL, 2.5 mmol) of 2-methylquinoline, and 2 mL of HFIP, and the reaction was allowed to proceed at 40° C. for 20 hours under a hydrogen pressure of 5 MPa. The conversion and the optical purity determined by GC analysis were 99.5% conv. (conversion) and 98.6% ee (optical purity).

Comparative Example 1

Hydrogenation Reaction of 2-Methylquinoline using RuBF$_4$((R,R)-Tsdpen) (p-cymene)

A reaction was carried out in the same manner as in Example 1, except that 3.4 mg (0.005 mmol, S/C=500) of RuBF$_4$((R,R)-Tsdpen) (p-cymene) was used as the catalyst. The conversion and the optical purity determined by GC analysis were 46.0% conv. (conversion) and 96.9% ee (optical purity).

The results of Example 1 and Comparative Example 1 are summarized as follows.

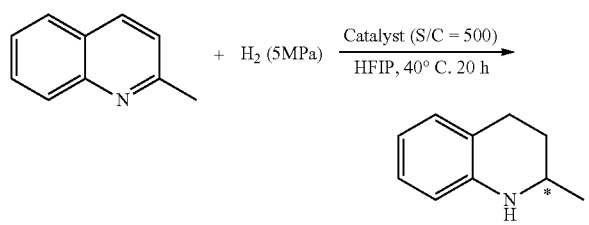

TABLE 1

|  | Catalyst | Conversion (%, conv) | Optical purity (%, ee) |
| --- | --- | --- | --- |
| Ex. 1 | RuBF$_4$((R,R)—N—Me-Tsdpen) (p-cymene) | 99.5 | 98.6 |
| Comp. Ex. 1 | RuBF$_4$((R,R)-Tsdpen) (p-cymene) | 46.0 | 96.9 |

As described above, the comparison with the conventionally used RuBF$_4$(Tsdpen) (p-cymene) complex used in the same catalytic amount showed that both the optical purity and the conversion were improved by the RuBF$_4$((R,R)—N-Me-Tsdpen) (p-cymene) complex of the present invention, and it can be seen that this complex of the present invention has a high activity and a high selectivisty.

Example 2

Hydrogenation Reaction of 2-Methylquinoline using RuOTf((R,R)—N-Me-Tsdpen) (p-cymene) (asymmetric reduction reaction of the present invention)

A 100 mL autoclave was charged with 3.8 mg (0.005 mmol, S/C=500) of RuOTf((R,R)—N-Me-Tsdpen) (p-cymene) obtained in Synthesis Example 4 serving as a catalyst, 0.358 g (0.34 mL, 2.5 mmol) of 2-methylquinoline, and 2 mL of HFIP, and the reaction was allowed to proceed at 40° C. for 6 hours under a hydrogen pressure of 5 MPa. The conversion and the optical purity determined by GC analysis were 91.0% conv. (conversion) and 97.4% ee (optical purity).

Comparative Example 2

Hydrogenation Reaction of 2-Methylquinoline using RuOTf((R,R)-Tsdpen) (p-cymene)

A reaction was carried out in the same manner as in Example 2, except that 3.4 mg (0.005 mmol, S/C=500) of RuOTf((R,R)-Tsdpen) (p-cymene) was used as the catalyst. The conversion and the optical purity determined by GC analysis were 51.4% conv. (conversion) and 95.0% ee (optical purity).

The results of Example 2 and Comparative Example 2 are summarized as follows.

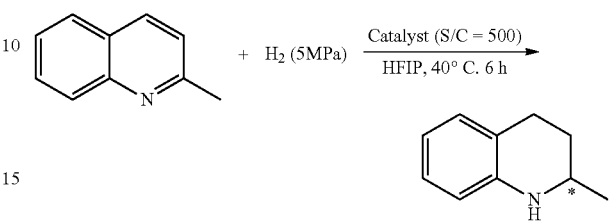

TABLE 2

|  | Catalyst | Conversion (%, conv) | Optical purity (%, ee) |
| --- | --- | --- | --- |
| Ex. 2 | RuOTf((R,R)—N—Me-Tsdpen) (p-cymene) | 91.0 | 97.4 |
| Comp. Ex. 2 | RuOTf((R,R)-Tsdpen) (p-cymene) | 51.4 | 95.0 |

As described above, the comparison with the conventionally used RuOTf(Tsdpen)(p-cymene) complex used in the same catalytic amount showed that both the optical purity and the conversion were improved by the RuOTf((R,R)—N-Me-Tsdpen) (p-cymene) complex of the present invention, and it can be seen that this complex of the present invention has a high activity and a high selectivity.

Example 3

Hydrogenation Reaction of 2-Methylquinoline using RuOTf ((R,R)—N-Me-Tsdpen) (p-cymene) (asymmetric reduction reaction of the present invention)

A 100 mL autoclave was charged with 7.6 mg (0.01 mmol, S/C=100) of RuOTf((R,R)—N-Me-Tsdpen) (p-cymene) obtained in Synthesis Example 4 serving as a catalyst, 0.143 g (0.14 mL, 1.0 mmol) of 2-methylquinoline, and 2 mL of methanol, and the reaction was allowed to proceed at 40° C. for 6 hours under a hydrogen pressure of 5 MPa. The conversion and the optical purity determined by GC analysis were 99.2% conv. (conversion) and 94.9% ee (optical purity).

Comparative Example 3

Hydrogenation Reaction of 2-Methylquinoline using RuOTf((R,R)-Tsdpen) (p-cymene)

A reaction was carried out in the same manner as in Example 3, except that 6.8 mg (0.01 mmol, S/C=100) of RuOTf((R,R)-Tsdpen) (p-cymene) was used as the catalyst. The conversion and the optical purity determined by GC analysis were 53.7% conv. (conversion) and 91.6% ee (optical purity).

The results of Example 3 and Comparative Example 3 are summarized as follows.

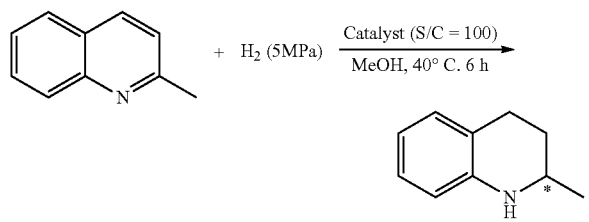

TABLE 3

| Catalyst | | Conversion (%, conv) | Optical purity (%, ee) |
|---|---|---|---|
| Ex. 3 | RuOTf((R,R)—N—Me-Tsdpen) (p-cymene) | 99.2 | 94.9 |
| Comp. Ex. 3 | RuOTf((R,R)-Tsdpen) (p-cymene) | 53.7 | 91.6 |

As described above, the comparison with the conventionally used RuOTf(Tsdpen)(p-cymene) complex used in the same catalytic amount showed that both the optical purity and the conversion were improved by the RuOTf((R,R)—N-Me-Tsdpen) (p-cymene) complex of the present invention, and it can be seen that this complex of the present invention has a high activity and a high selectivity.

Example 4

Hydrogenation Reaction of 2-Methylindole using RuBF$_4$ ((R,R)—N-Me-Tsdpen) (p-cymene) (asymmetric reduction reaction of the present invention)

A 100 mL autoclave was charged with 3.5 mg (0.005 mmol, S/C=1000) of RuBF$_4$((R,R)—N-Me-Tsdpen) (p-cymene) obtained in Synthesis Example 3 serving as a catalyst, 0.656 g (5 mmol) of 2-methylindole, and 2 mL of HFIP, and the reaction was allowed to proceed at 10° C. for 18 hours under a hydrogen pressure of 5 MPa. The conversion and the optical purity determined by GC analysis were 100% conv. (conversion) and 97.4% ee (optical purity).

Comparative Example 4

Hydrogenation Reaction of 2-Methylindole using RuBF$_4$((R,R)-Tsdpen) (p-cymene)

A reaction was carried out in the same manner as in Example 4, except that 3.4 mg (0.005 mmol, S/C=1000) of RuBF$_4$((R,R)-Tsdpen) (p-cymene) was used as the catalyst. The conversion and the optical purity determined by GC analysis were 85.2% conv. (conversion) and 94.5% ee (optical purity).

The results of Example 4 and Comparative Example 4 are summarized as follows.

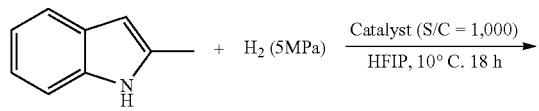

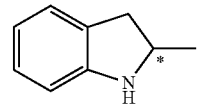

TABLE 4

| Catalyst | | Conversion (%, conv) | Optical purity (%, ee) |
|---|---|---|---|
| Ex. 4 | RuBF$_4$((R,R)—N—Me-Tsdpen) (p-cymene) | 100 | 97.4 |
| Comp. Ex. 4 | RuBF$_4$((R,R)-Tsdpen) (p-cymene) | 85.2 | 94.5 |

As described above, the comparison with the conventionally used RuBF$_4$(Tsdpen) (p-cymene) complex used in the same catalytic amount showed that both the optical purity and the conversion were improved by the RuBF$_4$((R,R)—N-Me-Tsdpen) (p-cymene) complex of the present invention, and it can be seen that this complex of the present invention has a high activity and a high selectivity.

Example 5

Hydrogenation Reaction of 2-Methylindole using RuOTf((R,R)—N-Me-Tsdpen) (p-cymene) (asymmetric reduction reaction of the present invention)

A 100 mL autoclave was charged with 3.8 mg (0.005 mmol, S/C=1000) of RuOTf((R,R)—N-Me-Tsdpen)(p-cymene) obtained in Synthesis Example 4 serving as a catalyst, 0.656 g (5 mmol) of 2-methylindole, and 2 mL of HFIP, and the reaction was allowed to proceed at 10° C. for 6 hours under a hydrogen pressure of 5 MPa. The conversion and the optical purity determined by GC analysis were 92.3% conv. (conversion) and 97.2% ee (optical purity).

Comparative Example 5

Hydrogenation Reaction of 2-Methylindole using RuOTf((R,R)-Tsdpen) (p-cymene)

A reaction was carried out in the same manner as in Example 5, except that 3.4 mg (0.005 mmol, S/C=1000) of RuOTf((R,R)-Tsdpen) (p-cymene) was used as the catalyst. The conversion and the optical purity determined by GC analysis were 69.2% conv. (conversion) and 95.1% ee (optical purity).

The results of Example 5 and Comparative Example 5 are summarized as follows.

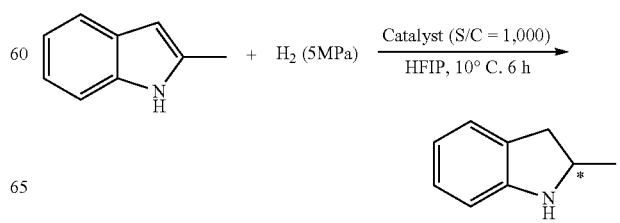

TABLE 5

| | Catalyst | Conversion (%, conv) | Optical purity (%, ee) |
|---|---|---|---|
| Ex. 5 | RuOTf((R,R)—N—Me-Tsdpen) (p-cymene) | 92.3 | 97.2 |
| Comp. Ex. 5 | RuOTf((R,R)-Tsdpen) (p-cymene) | 69.2 | 95.1 |

As described above, the comparison with the conventionally used RuOTf(Tsdpen)(p-cymene) complex used in the same catalytic amount showed that both the optical purity and the conversion were improved by the RuOTf((R,R)—N-Me-Tsdpen) (p-cymene) complex of the present invention, and it can be seen that this complex of the present invention has a high activity and a high selectivity.

Example 6

Hydrogenation Reaction of 2-Methylquinoxaline using RuOTf ((R,R)—N-Me-Tsdpen) (p-cymene) (asymmetric reduction reaction of the present invention)

A 100 mL autoclave was charged with 7.6 mg (0.01 mmol, S/C=100) of RuOTf((R,R)—N-Me-Tsdpen)(p-cymene) obtained in Synthesis Example 4 serving as a catalyst, 0.144 g (0.13 mL, 1.0 mmol) of 2-methylquinoxaline, and 1 mL of HFIP, and the reaction was allowed to proceed at 40° C. for 6 hours under a hydrogen pressure of 5 MPa. The conversion and the optical purity determined by GC analysis were 76.7% conv. (conversion) and 88.3% ee (optical purity).

Comparative Example 6

Hydrogenation Reaction of 2-Methylquinoxaline using RuOTf((R,R)-Tsdpen) (p-cymene)

A reaction was carried out in the same manner as in Example 6, except that 6.8 mg (0.01 mmol, S/C=100) of RuOTf((R,R)-Tsdpen) (p-cymene) was used as the catalyst. The conversion and the optical purity determined by GC analysis were 41.8% conv. (conversion) and 86.9% ee (optical purity).

The results of Example 6 and Comparative Example 6 are summarized as follows.

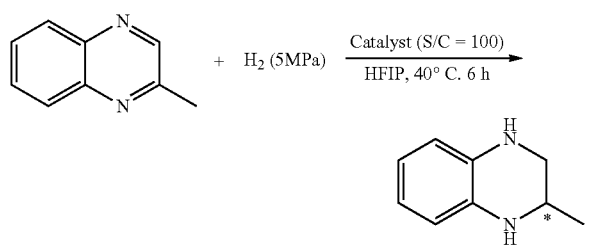

TABLE 6

| | Catalyst | Conversion (%, conv) | Optical purity (%, ee) |
|---|---|---|---|
| Ex. 6 | RuOTf((R,R)—N—Me-Tsdpen) (p-cymene) | 76.7 | 88.3 |
| Comp. Ex. 6 | RuOTf((R,R)-Tsdpen) (p-cymene) | 41.8 | 86.9 |

As described above, the comparison with the conventionally used RuOTf(Tsdpen)(p-cymene) complex used in the same catalytic amount showed that both the optical purity and the conversion were improved by the RuOTf((R,R)—N-Me-Tsdpen) (p-cymene) complex of the present invention, and it can be seen that this complex of the present invention has a high activity and a high selectivity.

Example 7

Hydrogenation Reaction of 2-Methylquinoxaline using $RuBF_4$((R,R)—N-Me-Tsdpen) (p-cymene) (asymmetric reduction reaction of the present invention)

A 100 mL autoclave was charged with 3.8 mg (0.005 mmol, S/C=200) of ($RuBF_4$((R,R)—N-Me-Tsdpen) (p-cymene) obtained in Synthesis Example 3 serving as a catalyst, 0.144 g (0.13 mL, 1.0 mmol) of 2-methylquinoxaline, and 2 mL of dichloromethane, and the reaction was allowed to proceed at 40° C. for 6 hours under a hydrogen pressure of 5 MPa. The conversion and the optical purity determined by GC analysis were 71.2% conv. (conversion) and 86.5% ee (optical purity).

Comparative Example 7

Hydrogenation Reaction of 2-Methylquinoxaline using $RuBF_4$((R,R)-Tsdpen) (p-cymene)

A reaction was carried out in the same manner as in Example 7, except that 3.5 mg (0.005 mmol, S/C=200) of $RuBF_4$((R,R)-Tsdpen) (p-cymene) was used as the catalyst. The conversion and the optical purity determined by GC analysis were 11.8% conv. (conversion) and 74.9% ee (optical purity).

The results of Example 7 and Comparative Example 7 are summarized as follows.

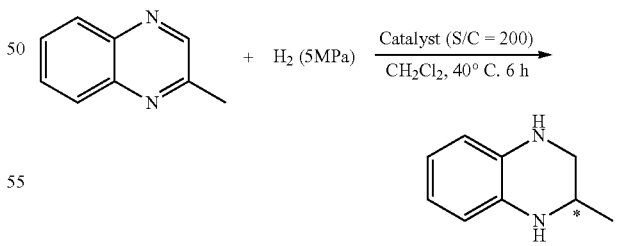

TABLE 7

| | Catalyst | Conversion (%, conv) | Optical purity (%, ee) |
|---|---|---|---|
| Ex. 7 | $RuBF_4$((R,R)—N—Me-Tsdpen) (p-cymene) | 71.2 | 86.5 |

TABLE 7-continued

|  | Catalyst | Conversion (%, conv) | Optical purity (%, ee) |
|---|---|---|---|
| Comp. Ex. 7 | RuBF$_4$(R,R)-Tsdpen) (p-cymene) | 11.8 | 74.9 |

As described above, the comparison with the conventionally used RuBF$_4$(Tsdpen) (p-cymene) complex used in the same catalytic amount showed that both the optical purity and the conversion were improved by the RuBF$_4$((R,R)—N-Me-Tsdpen) (p-cymene) complex of the present invention, and it can be seen that this complex of the present invention has a high activity and a high selectivity.

Example 8

Hydrogenation Reaction of 2,3,3-Trimethylindolenine using RuBF$_4$ ((R,R)—N-Me-Tsdpen) (p-cymene) (asymmetric reduction reaction of the present invention)

A 100 mL autoclave was charged with 3.8 mg (0.005 mmol, S/C=300) of RuBF$_4$((R,R)—N-Me-Tsdpen) (p-cymene) obtained in Synthesis Example 3 serving as a catalyst, 0.239 g (0.24 mL, 1.5 mmol) of 2,3,3-trimethylindolenine, and 1 mL of HFIP, and the reaction was allowed to proceed at 50° C. for 6 hours under a hydrogen pressure of 5 MPa. The conversion and the optical purity determined by GC analysis were 99.2% conv. (conversion) and 95.8% ee (optical purity).

Comparative Example 8

Hydrogenation Reaction of 2,3,3-Trimethylindolenine using RuBF$_4$((R,R)-Tsdpen) (p-cymene)

A reaction was carried out in the same manner as in Example 8, except that 3.4 mg (0.005 mmol, S/C=300) of RuBF$_4$((R,R)-Tsdpen) (p-cymene) was used as the catalyst. The conversion and the optical purity determined by GC analysis were 1.7% conv. (conversion) and 48.5% ee (optical purity).

The results of Example 8 and Comparative Example 8 are summarized as follows.

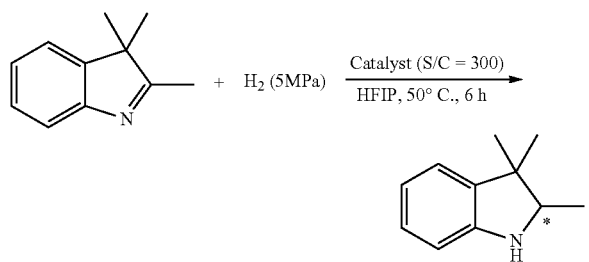

TABLE 8

|  | Catalyst | Conversion (%, conv) | Optical purity (%, ee) |
|---|---|---|---|
| Ex. 8 | RuBF$_4$((R,R)—N—Me-Tsdpen) (p-cymene) | 99.2 | 95.8 |

TABLE 8-continued

|  | Catalyst | Conversion (%, conv) | Optical purity (%, ee) |
|---|---|---|---|
| Comp. Ex. 8 | RuBF$_4$((R,R)-Tsdpen) (p-cymene) | 1.7 | 48.5 |

As described above, the comparison with the conventionally used RuBF$_4$(Tsdpen) (p-cymene) complex used in the same catalytic amount showed that both the optical purity and the conversion were improved by the RuBF$_4$((R,R)—N-Me-Tsdpen) (p-cymene) complex of the present invention, and it can be seen that this complex of the present invention has a high activity and a high selectivity.

Example 9

Hydrogenation Reaction of 2,3,3-Trimethylindolenine using RuBF$_4$((R,R)—N-Me-Tsdpen) (p-cymene) (asymmetric reduction reaction of the present invention)

A 100 mL autoclave was charged with 3.8 mg (0.005 mmol, S/C=200) of RuBF$_4$((R,R)—N-Me-Tsdpen) (p-cymene) obtained in Synthesis Example 3 serving as a catalyst, 0.159 g (0.16 mL, 1.0 mmol) of 2,3,3-trimethylindolenine, and 2 mL of dichloromethane, and the reaction was allowed to proceed at 50° C. for 6 hours under a hydrogen pressure of 5 MPa. The conversion and the optical purity determined by GC analysis were 99.7% conv. (conversion) and 94.6% ee (optical purity).

Comparative Example 9

Hydrogenation Reaction of 2,3,3-Trimethylindolenine using RuBF$_4$ ((R,R)-Tsdpen) (p-cymene)

A reaction was carried out in the same manner as in Example 9, except that 3.4 mg (0.005 mmol, S/C=200) of RuBF$_4$((R,R)-Tsdpen) (p-cymene) was used as the catalyst. The conversion and the optical purity determined by GC analysis were 21.2% conv. (conversion) and 84.4% ee (optical purity).

The results of Example 9 and Comparative Example 9 are summarized as follows.

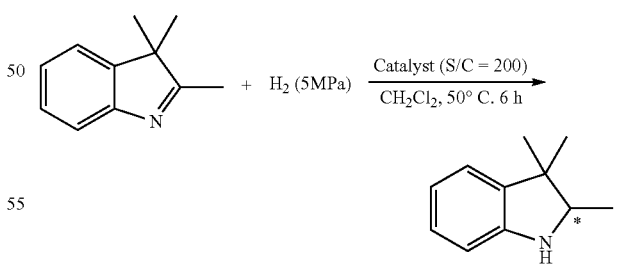

TABLE 9

|  | Catalyst | Conversion (%, conv) | Optical purity (%, ee) |
|---|---|---|---|
| Ex. 9 | RuBF$_4$((R,R)—N—Me-Tsdpen) (p-cymene) | 99.7 | 94.6 |

TABLE 9-continued

| Catalyst | | Conversion (%, conv) | Optical purity (%, ee) |
|---|---|---|---|
| Comp. Ex. 9 | RuBF$_4$((R,R)-Tsdpen) (p-cymene) | 21.2 | 84.4 |

As described above, the comparison with the conventionally used RuBF$_4$(Tsdpen)(p-cymene) complex used in the same catalytic amount showed that both the optical purity and the conversion were improved by the RuBF$_4$((R,R)—N-Me-Tsdpen) (p-cymene) complex of the present invention, and it can be seen that this complex of the present invention has a high activity and a high selectivity.

Example 10

Hydrogenation Reaction of 2,3,3-Trimethylindolenine using RuBF$_4$((R,R)—N-Me-Tsdpen) (p-cymene) (asymmetric reduction reaction of the present invention)

A 100 mL autoclave was charged with 3.8 mg (0.005 mmol, S/C=200) of RuBF$_4$((R,R)—N-Me-Tsdpen) (p-cymene) obtained in Synthesis Example 3 serving as a catalyst, 0.159 g (0.16 mL, 1.0 mmol) of 2,3,3-trimethylindolenine, and 2 mL of THF, and the reaction was allowed to proceed at 50° C. for 6 hours under a hydrogen pressure of 5 MPa. The conversion and the optical purity determined by GC analysis were 76.4% conv. (conversion) and 87.4% ee (optical purity).

Comparative Example 10

Hydrogenation Reaction of 2,3,3-Trimethylindolenine using RuBF$_4$((R,R)-Tsdpen) (p-cymene)

A reaction was carried out in the same manner as in Example 10, except that 3.4 mg (0.005 mmol, S/C=200) of RuBF$_4$((R,R)-Tsdpen) (p-cymene) was used as the catalyst. The conversion and the optical purity determined by GC analysis were 41.9% conv. (conversion) and 85.9% ee (optical purity).

The results of Example 10 and Comparative Example 10 are summarized as follows.

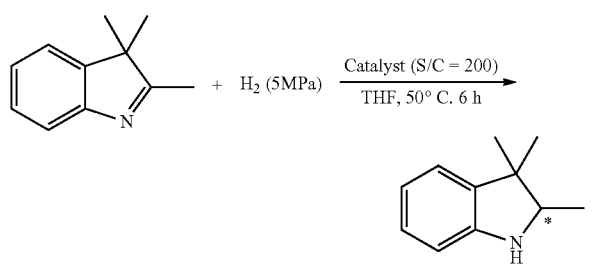

TABLE 10

| Catalyst | | Conversion (%, conv) | Optical purity (%, ee) |
|---|---|---|---|
| Ex. 10 | RuBE$_4$((R,R)—N—Me-Tsdpen) (p-cymene) | 76.4 | 87.4 |

TABLE 10-continued

| Catalyst | | Conversion (%, conv) | Optical purity (%, ee) |
|---|---|---|---|
| Comp. Ex. 10 | RuBF$_4$((R,R)-Tsdpen) (p-cymene) | 41.9 | 85.9 |

As described above, the comparison with the conventionally used RuBF$_4$(Tsdpen) (p-cymene) complex used in the same catalytic amount showed that both the optical purity and the conversion were improved by the RuBF$_4$((R,R)—N-Me-Tsdpen) (p-cymene) complex of the present invention, and it can be seen that this complex of the present invention has a high activity and a high selectivity.

Example 11

Hydrogenation Reaction of 4-Methoxy-N-(4-methylpentan-2-ylidene)aniline using RuBF$_4$((R,R)—N-Me-Tsdpen) (p-cymene) (asymmetric reduction reaction of the present invention)

A 100 mL autoclave was charged with 7.6 mg (0.01 mmol, S/C=100) of RuBF$_4$((R,R)—N-Me-Tsdpen) (p-cymene) obtained in Synthesis Example 3 serving as a catalyst, 0.205 g (1.0 mmol) of 4-methoxy-N— (4-methylpentan-2-ylidene) aniline, and 2 mL of dichloromethane, and the reaction was allowed to proceed at 40° C. for 6 hours under a hydrogen pressure of 5 MPa. The conversion determined by GC analysis and the optical purity determined by HPLC analysis were 50.4% conv. (conversion) and 47% ee (optical purity).

Comparative Example 11

Hydrogenation Reaction of 4-Methoxy-N-(4-methylpentan-2-ylidene)aniline using RuBF$_4$ ((R,R)-Tsdpen) (p-cymene)

A reaction was carried out in the same manner as in Example 11, except that 6.8 mg (0.01 mmol, S/C=100) of RuBF$_4$((R,R)-Tsdpen) (p-cymene) was used as the catalyst. The conversion and the optical purity determined by GC analysis were 36.7% conv. (conversion) and 21% ee (optical purity).

The results of Example 11 and Comparative Example 11 are summarized as follows.

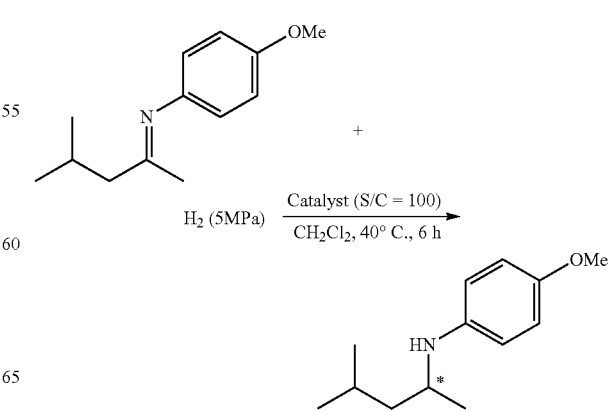

TABLE 11

| | Catalyst | Conversion (%, conv) | Optical purity (%, ee) |
|---|---|---|---|
| Ex. 11 | RuBF$_4$((R,R)—N—Me-Tsdpen) (p-cymene) | 50.4 | 47 |
| Comp. Ex. 11 | RuBE$_4$((R,R)-Tsdpen) (p-cymene) | 36.7 | 21 |

As described above, the comparison with the conventionally used RuBF$_4$(Tsdpen) (p-cymene) complex used in the same catalytic amount showed that both the optical purity and the conversion were improved by the RuBF$_4$((R,R)—N-Me-Tsdpen) (p-cymene) complex of the present invention, and it can be seen that this complex of the present invention has a high activity and a high selectivity.

Example 12

Hydrogenation Reaction of 3-Methyl-2H-benzo[1,4]oxazine using RuBF$_4$ ((R,R)—N-Me-Tsdpen) (p-cymene) (asymmetric reduction reaction of the present invention)

A 100 mL autoclave was charged with 7.6 mg (0.01 mmol, S/C=100) of RuBF$_4$((R,R)—N-Me-Tsdpen) (p-cymene) obtained in Synthesis Example 3 serving as a catalyst, 0.147 g (1.0 mmol) of 3-methyl-2H-benzo[1,4]oxazine, and 2 mL of HFIP, and the reaction was allowed to proceed at 40° C. for 6 hours under a hydrogen pressure of 5 MPa. The conversion determined by GC analysis and the optical purity determined by HPLC analysis were >99% conv. (conversion) and 78% ee (optical purity).

Comparative Example 12

Hydrogenation Reaction of 3-Methyl-2H-benzo[1,4]oxazine using RuBF$_4$ ((R,R)-Tsdpen) (p-cymene)

A reaction was carried out in the same manner as in Example 12, except that 6.8 mg (0.01 mmol, S/C=100) of RuBF$_4$((R,R)-Tsdpen) (p-cymene) was used as the catalyst. The conversion and the optical purity determined by GC analysis were >99% conv. (conversion) and 72% ee (optical purity).

The results of Example 12 and Comparative Example 12 are summarized as follows.

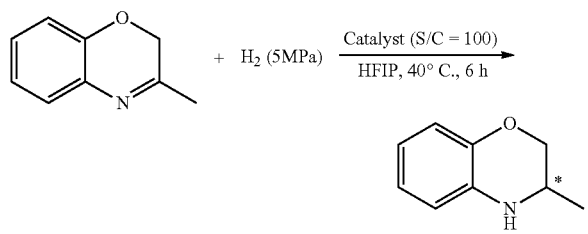

TABLE 12

| | Catalyst | Conversion (%, conv) | Optical purity (%, ee) |
|---|---|---|---|
| Ex. 12 | RuBF$_4$((R,R)—N—Me-Tsdpen) (p-cymene) | >99 | 78 |
| Comp. Ex. 12 | RuBF$_4$((R,R)-Tsdpen) (p-cymene) | >99 | 12 |

As described above, the comparison with the conventionally used RuBF$_4$(Tsdpen) (p-cymene) complex used in the same catalytic amount showed that the optical purity was improved by the RuBF$_4$((R,R)—N-Me-Tsdpen) (p-cymene) complex of the present invention, and it can be seen that this complex of the present invention has a high selectivity.

Comparative Example 13

Hydrogen Transfer Reaction of 2-Methylquinoline using RuBF$_4$((R,R)—N-Me-Tsdpen) (p-cymene) and using Formic Acid as Hydrogen Source A 15 mL Schlenk tube was charged with 3.5 mg (0.005 mmol, S/C=500) of RuBF$_4$((R,R)—N-Me-Tsdpen) (p-cymene) obtained in Synthesis Example 3 serving as a catalyst, 0.358 g (0.34 mL, 2.5 mmol) of 2-methylquinoline, and 1.25 mL of formic acid-triethylamine (formic acid:triethylamine=5:2 azeotrope), and the reaction was allowed to proceed at 40° C. for 20 hours. The conversion and the optical purity determined by GC analysis were 17.5% conv. (conversion) and 69.1% ee (optical purity).

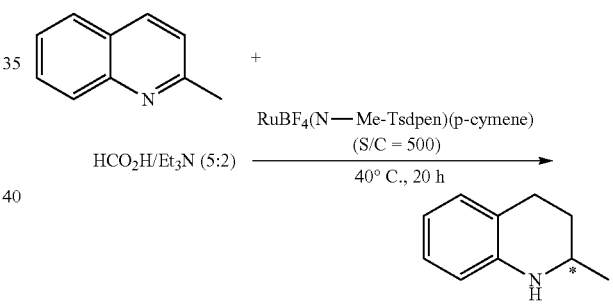

As described above, it can be seen that both the conversion and the optical purity are remarkably lower in the reduction of 2-methylquinoline using RuBF$_4$ ((R,R)—N-Me-Tsdpen) (p-cymene) of the present invention under typical reaction conditions for the conventionally and widely used hydrogen transfer-type reaction using formic acid as a hydrogen source than in a hydrogenation reaction using hydrogen gas as a hydrogen source as in Example 1. This indicates that the reduction method using the catalyst of the invention and using hydrogen gas as a hydrogen source is very effective.

Comparative Example 14

Hydrogen Transfer Reaction of 2-Methylindole using RuBF$_4$((R,R)—N-Me-Tsdpen) (p-cymene) and using Formic acid as Hydrogen Source A 15 mL Schlenk tube was charged with 3.5 mg (0.005 mmol, S/C=1000) of RuBF$_4$((R,R)—N-Me-Tsdpen) (p-cymene) obtained in Synthesis Example 3 serving as a catalyst, 0.656 g (5.0 mmol) of 2-methylindole, and 2.5 mL of formic acid-triethylamine (formic acid:triethylamine=5:2 azeotrope), and the reaction was allowed to proceed at 10° C. for 18 hours. The conversion and the optical purity were analyzed by GC, but the reaction did not proceed at all.

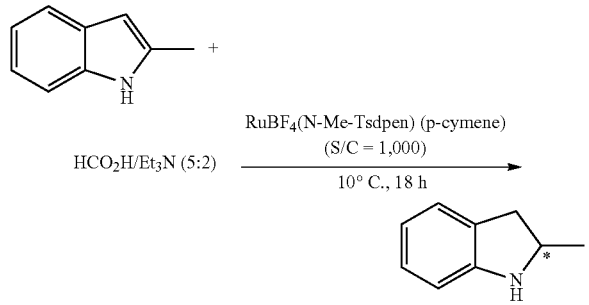

As described above, the reaction did not proceed when 2-methylindole was reduced by using RuBF$_4$((R,R)—N-Me-Tsdpen) (p-cymene) of the present invention under typical reaction conditions of the conventionally and widely used hydrogen transfer-type reaction using formic acid as a hydrogen source. On the other hand, a high conversion and a high optical purity can be obtained in a hydrogenation reaction using hydrogen gas as a hydrogen source as in Example 4. Hence, it can be seen that the reduction method using the catalyst of the invention and using hydrogen gas as a hydrogen source is very effective.

Comparative Example 15

Hydrogen Transfer Reaction of 2-Methylquinoxaline using RuBF$_4$((R,R)—N-Me-Tsdpen) (p-cymene) and using Formic Acid as Hydrogen Source A 15 mL Schlenk tube was charged with 3.5 mg (0.005 mmol, S/C=200) of RuBF$_4$((R,R)—N-Me-Tsdpen) (p-cymene) obtained in Synthesis Example 3 serving as a catalyst, 0.144 g (0.128 mL, 1.0 mmol) of 2-methylquinoxaline, and 0.5 mL of formic acid-triethylamine (formic acid:triethylamine=5:2 azeotrope), and the reaction was allowed to proceed at 40° C. for 6 hours. The conversion and the optical purity determined by GC analysis were 31.9% conv. (conversion) and 85.7% ee (optical purity).

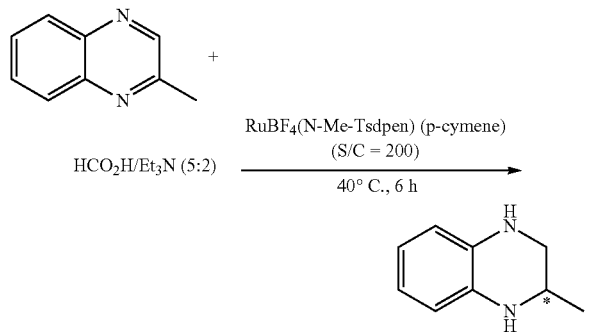

As described above, it can be seen that the conversion was remarkably lower in the reduction of 2-methylquinoxaline using RuBF$_4$((R,R)—N-Me-Tsdpen) (p-cymene) of the present invention under typical reaction conditions of the conventionally and widely used hydrogen transfer-type reaction using formic acid as a hydrogen source than in the hydrogenation reaction using hydrogen gas as a hydrogen source as in Example 7. This indicates that the reduction method using the catalyst of the invention and using hydrogen gas as a hydrogen source is very effective.

Comparative Example 16

Hydrogen Transfer Reaction of 2,3,3-Trimethylindolenine using RuBF$_4$((R,R)—N-Me-Tsdpen) (p-cymene) and using Formic Acid as Hydrogen Source A 15 mL Schlenk tube was charged with 7.0 mg (0.01 mmol, S/C=200) of RuBF$_4$((R,R)—N-Me-Tsdpen) (p-cymene) obtained in Synthesis Example 3 serving as a catalyst, 0.318 g (0.32 mL, 2.0 mmol) of 2,3,3-trimethylindolenine, and 1.0 mL of formic acid-triethylamine (formic acid:triethylamine=5:2 azeotrope), and the reaction was allowed to proceed at 50° C. for 6 hours. The conversion and the optical purity determined by GC analysis were 20.4% conv. (conversion) and 14.9% ee (optical purity)

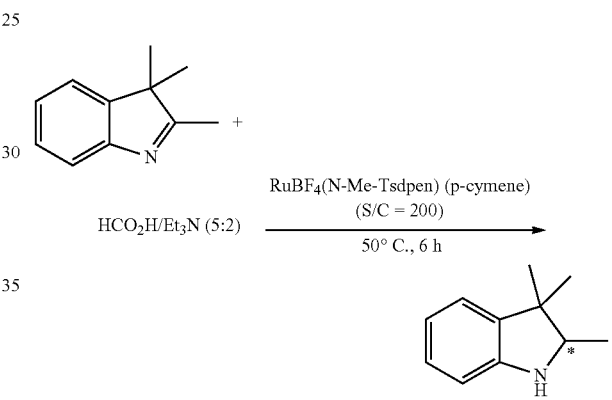

As described above, it can be seen that the reduction of 2,3,3-trimethylindolenine using RuBF$_4$((R,R)—N-Me-Tsdpen) (p-cymene) of the present invention under typical reaction conditions of the conventionally and widely used hydrogen transfer-type reaction using formic acid as a hydrogen source did not achieve a good conversion or a good optical purity, and both the conversion and the optical purity were remarkably lower in this reduction than in the hydrogenation reactions using hydrogen gas as a hydrogen source as in Examples 8, 9, and 10. This indicates that the reduction method using the catalyst of the invention and using hydrogen gas as a hydrogen source is very effective.

Synthesis Example 10

Synthesis of Iridium Complex (Cp*IrCl((R,R)—N-Me-Tsdpen)) (iridium complex of general formula (3))

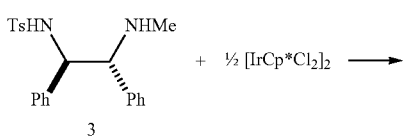

-continued

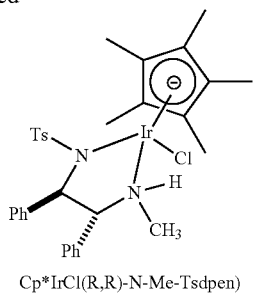

Cp*IrCl(R,R)-N-Me-Tsdpen)

In 15 mL of dichloromethane, 0.50 g (1.314 mmol) of Compound 3 obtained in Synthesis Example 1, 0.524 g (1.314 mmol) of [IrCp*Cl$_2$]z, and 0.266 g (0.366 mL, 2.628 mmol) of triethylamine were dissolved, and the reaction was allowed to proceed at room temperature for 40 minutes. After that, the solvent was recovered from the reaction liquid, followed by purification by silica gel column chromatography (chloroform:methanol=20:1 (volume ratio)). Thus, 0.976 g of Cp*IrCl((R,R)—N-Me-Tsdpen), which is an iridium complex of the present invention, was obtained (Yield: 100%).

$^1$H-NMR (CDCl$_2$, 300 MHz): δ 7.62-7.58 (d, 2H), 7.20-6.63 (m, 12H), 4.50-4.40 (brs, 1H), 4.40 (d, 1H), 3.60 (t, 1H), 2.62 (d, 3H), 2.24 (s, 3H), 1.80 (s, 15H);

HRMS (ESI) calcd for C$_{32}$H$_{38}$IrN$_2$O$_2$S [M-Cl]$^+$ 707.2283, found 707.2280.

Synthesis Example 11

Synthesis of Iridium Complex (Cp*IrBF$_4$((R,R)—N-Me-Tsdpen)) (iridium complex of general formula (4))

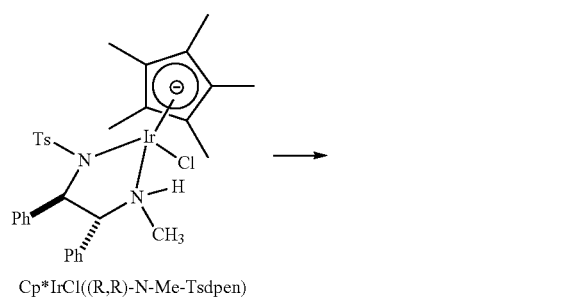

Cp*IrCl((R,R)-N-Me-Tsdpen)

Cp*IrBF$_4$((R,R)-N-Me-Tsdpen)

In 6 mL of methanol and 6 mL of dichloromethane, 0.5 g (0.672 mmol) of the iridium complex, Cp*IrCl((R,R)—N-Me-Tsdpen), obtained in Synthesis Example 10 and 0.157 g (0.807 mmol) of AgBF$_4$ were stirred for 1 hour. After the precipitated salt was filtered through Celite, the filtrate was concentrated using an evaporator and dried under reduced pressure. Thus, 0.53 g of Cp*IrBF$_4$((R,R)—N-Me-Tsdpen), which is an iridium complex of the present invention, was obtained (Yield: 99%).

$^1$H-NMR (CD$_3$OD, 300 MHz): δ 7.30-6.95 (m, 14H), 4.75 (d, 0.67H), 4.70 (m, 0.33H), 4.25 (m, 0.33H), 4.00 (d, 0.66H), 2.85 (s, 1H), 2.69 (s, 2H), 2.29 (s, 2H), 2.26 (s, 1H), 1.90 (s, 5H), 1.88 (s, 10H);

HRMS (ESI) calcd for C$_{32}$H$_{38}$IrN$_2$O$_2$S [M-BF$_4$]$^+$ 707.2283, found 707.2273.

Synthesis Example 12

Synthesis of Ruthenium Complex (RuCl((R,R)—N-Me-Tsdpen) (mesitylene)) (ruthenium complex of general formula (2))

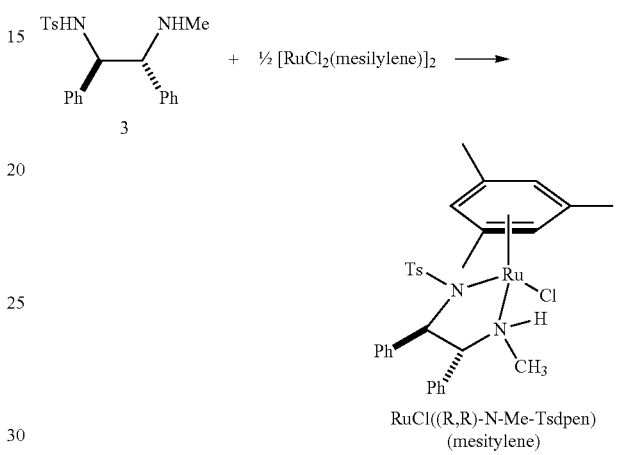

RuCl((R,R)-N-Me-Tsdpen) (mesitylene)

In 20 mL of 2-propanol, Compound 3 (1.0 g, 2.628 mmol) obtained in Synthesis Example 1, [RuCl$_2$(mesitylene)]$_2$ (0.759 g, 2.628 mmol (in terms of Ru)), and 0.531 g (0.74 mL, 5.256 mmol) of triethylamine were dissolved, and the reaction was allowed to proceed at 80° C. for 1.5 hours. After that, the solvent was recovered from the reaction liquid, and 50 mL of water was added, followed by stirring for 10 minutes under ice-cooling. The precipitated crystals were filtered, and then dried under reduced pressure. Thus, 1.54 g of RuCl((R,R)—N-Me-Tsdpen) (mesitylene) was obtained (Yield: 93.3%).

$^1$H-NMR (CD$_2$Cl$_2$, 400 MHz): δ7.25-7.10 (m, 6H), 6.90-6.62 (m, 8H), 5.43 (s, 3H), 3.93 (d, 1H), 3.85 (brs, 1H), 3.60 (t, 1H), 2.72 (d, 3H), 2.35 (s, 9H), 2.25 (s, 3H);

HRMS (ESI) calcd for C$_{31}$H$_{35}$N$_2$O$_2$RuS [M-Cl]$^+$ 601.1463, found 601.1454.

Synthesis Example 13

Synthesis of Ruthenium Complex (RuBF$_4$((R,R)—N-Me-Tsdpen) (mesitylene)) (ruthenium complex of general formula (1))

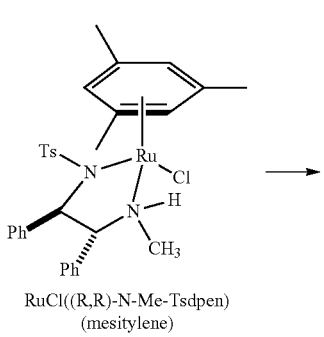

RuCl((R,R)-N-Me-Tsdpen) (mesitylene)

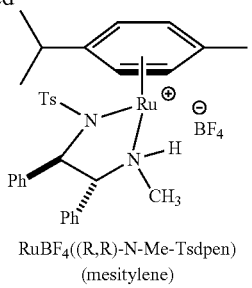

RuBF$_4$((R,R)-N-Me-Tsdpen)
(mesitylene)

In 5 mL of methanol and 10 mL of dichloromethane, 1.15 g (1.80 mmol) of the ruthenium complex, RuCl((R,R)—N-Me-Tsdpen) (mesitylene), obtained in Synthesis Example 12 and 0.409 g (2.10 mmol) of AgBF$_4$ were stirred for 2 hours. After the precipitated salt was filtered through Celite, the filtrate was concentrated using an evaporator and dried under reduced pressure. Thus, 1.23 g of RuBF$_4$((R,R)—N-Me-Tsdpen) (mesitylene), which is a ruthenium complex of the present invention, was obtained (Yield: 99%).

$^1$H-NMR (CD$_3$OD, 400 MHz): δ 7.50-6.65 (m, 14H), 5.82 (s, 3H), 4.19 (d, 1H), 3.84 (d, 1H), 2.97 (s, 3H), 2.34 (s, 9H), 2.20 (s, 3H);

HRMS (ESI) calcd for C$_{31}$H$_{35}$N$_2$O$_2$RuS [M-BF$_4$]$^+$ 601.1463, found 601.1475.

Synthesis Example 14

Synthesis of Ruthenium Complex (RuCl((R,R)—N-Me-Tsdpen) (benzene)) (ruthenium complex of general formula (2))

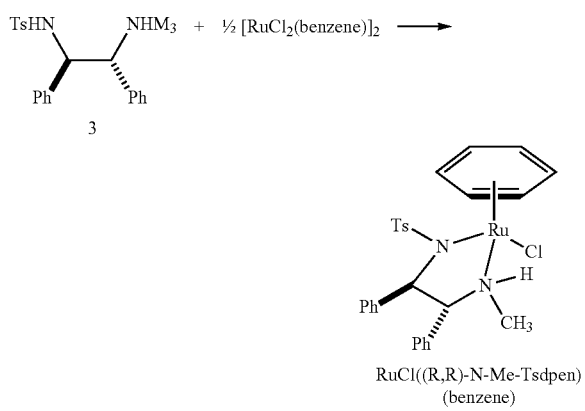

RuCl((R,R)-N-Me-Tsdpen)
(benzene)

In 15 mL of 2-propanol, Compound 3 (1.0 g, 2.628 mmol) obtained in Synthesis Example 1, [RuCl$_2$(benzene)]$_2$ (0.65 g, 2.628 mmol (in terms of Ru)), and 0.531 g (0.74 mL, 5.256 mmol) of triethylamine were dissolved, and the reaction was allowed to proceed at 80° C. for 1 hour. After that, the solvent was recovered from the reaction liquid, and 50 mL of water was added, followed by stirring for 10 minutes under ice-cooling. The precipitated crystals were filtered, and then dried under reduced pressure. Thus, 1.54 g of RuCl((R,R)—N-Me-Tsdpen) (benzene) was obtained (Yield: 94.2%).

$^1$H-NMR (CD$_2$Cl$_2$, 400 MHz): δ 7.20-7.10 (m, 5H), 6.88-6.60 (m, 9H), 5.81 (s, 6H), 4.05 (d, 1H), 3.95 (brs, 1H), 3.70 (t, 1H), 2.89 (d, 3H), 2.27 (s, 3H);

HRMS (ESI) calcd for C$_{28}$H$_{29}$N$_2$O$_2$RuS [M-Cl]; 559.0993, found 559.0090.

Synthesis Example 15

Synthesis of Ruthenium Complex (RuBF$_4$((R,R)—N-Me-Tsdpen) (benzene)) (ruthenium complex of general formula (1))

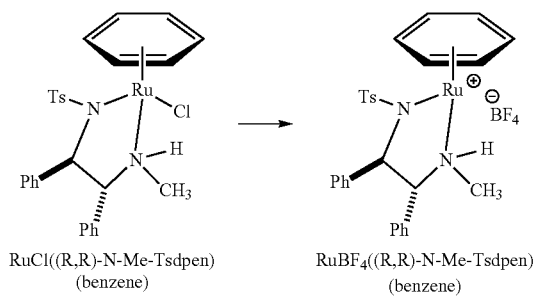

RuCl((R,R)-N-Me-Tsdpen)    RuBF$_4$((R,R)-N-Me-Tsdpen)
(benzene)                  (benzene)

In 5 mL of methanol and 20 mL of dichloromethane, 1.11 g (1.80 mmol) of the ruthenium complex, RuCl((R,R)—N-Me-Tsdpen) (benzene), obtained in Synthesis Example 14 and 0.409 g (2.10 mmol) of AgBF$_4$ were stirred for 2 hours. After the precipitated salt was filtered through Celite, the filtrate was concentrated using an evaporator and dried under reduced pressure. Thus, 1.15 g of RuBF$_4$((R,R)—N-Me-Tsdpen) (benzene), which is a ruthenium complex of the present invention, was obtained (Yield: 99%).

$^1$H-NMR (CD$_3$OD, 400 MHz): δ 7.21-6.57 (m, 14H), 6.07 (s, 6H), 4.21 (d, 1H), 3.79 (d, 1H), 2.99 (s, 3H), 2.23 (s, 3H);

HRMS (ESI) calcd for C$_{28}$H$_{29}$N$_2$O$_2$RuS [M-BF$_4$]; 559.0993, found 559.0983.

Synthesis Example 16

Synthesis of (1S,2S)—N-Me-MsDPEN (Compound 7) (synthesis of diamine compound usable for synthesis of complexes of general formulae (1) to (4))

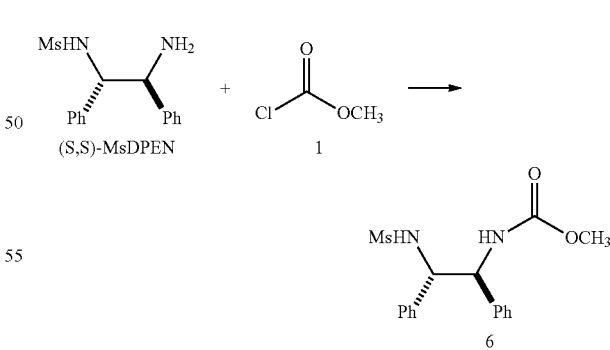

A three-way stopcock, a stir bar, a dropping funnel, and a thermometer were attached to a 500 mL 4-necked reaction flask, and the inside of the reaction flask was purged with nitrogen. To this reaction flask, 5.0 g (17.22 mmol) of (S,S)-MsDPEN, 3.25 g (2.66 mL, 34.43 mmol) of methyl chloroformate (Compound 1), 7.13 g (51.65 mmol) of potassium carbonate, 34.5 mL of water, and 34.35 mL of THF were added under a nitrogen stream, followed by stirring at room temperature for 1 hour. The conversion was checked by TLC, and the raw material had been disappeared. At this time point, the reaction was terminated, and 100 mL of toluene and 35 mL of water were added followed by stirring. Then, after the mixture was allowed to stand, the aqueous layer was removed. The obtained organic layer was directly concentrated to dryness by removing the solvent using an evaporator. Thus, 6.0 g of almost pure Compound 6, (N-((1S,2S)-2-methanesulfonamide-1,2-diphenylethyl) acetamide), was obtained. This compound was used in the subsequent reaction without further purification.

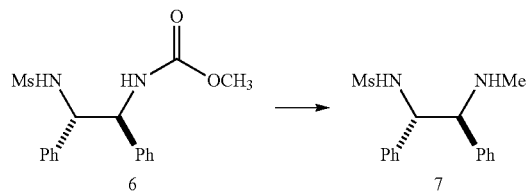

To the entire amount of the obtained Compound 6, 345 mL of toluene and 14.9 g (13.3 mL, 51.65 mmol) of Vitride (registered trademark) (70% toluene solution), which was a reducing agent, were added, and the reaction was allowed to proceed in an oil bath at 120° C. under reflux for 1 hour. The conversion was checked by TLC, and the raw material had disappeared. At this time point, the reaction was terminated, and 10 mL of water was slowly added to the reaction liquid under ice-cooling. After that, 100 mL of water was further added, and the mixture was stirred and allowed to stand. Then, the aqueous layer was separated. After this washing operation was repeated twice, the solvent in the organic layer was recovered using an evaporator, and the obtained concentrate was purified by silica gel column chromatography. Thus, 2.06 g of Compound 7 (diamine compound) was obtained (Yield: 39.4%).

$^1$H-NMR (CDCl$_3$, 400 MHz): δ 7.40-7.18 (m, 10H), 5.34 (brs, 1H), 4.68 (d, 1H), 4.02 (d, 1H), 2.39 (s, 3H), 2.35 (s, 3H);

HRMS (ESI) calcd for C$_{10}$H$_{21}$N$_2$O$_2$S [M+H]+ 305.1324, found 305.1322.

Synthesis Example 17

Synthesis of Ruthenium Complex (RuCl((S,S)—N-Me-Msdpen) (p-cymene)) (ruthenium complex of general formula (2))

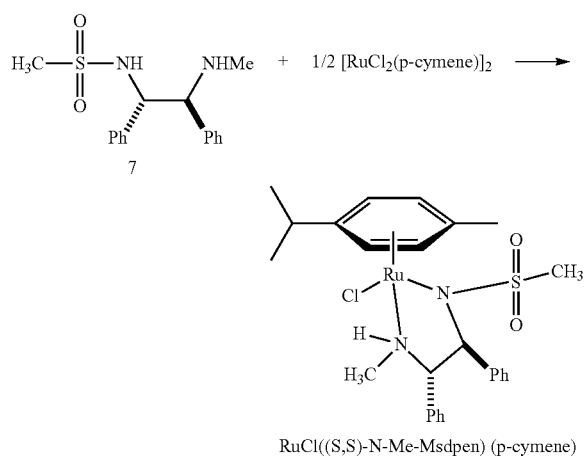

RuCl((S,S)-N-Me-Msdpen) (p-cymene)

In 15 mL of 2-propanol, Compound 7 (0.6 g, 1.90 mmol) obtained in Synthesis Example 16, [RuCl$_2$(p-cymene)]$_2$ (0.581 g, 1.90 mmol (in terms of Ru)), and 0.385 g (0.54 mL, 3.8 mmol) of triethylamine were dissolved, and the reaction was allowed to proceed at 80° C. for 1.5 hours. After that, the solvent was recovered from the reaction liquid, and 15 mL of water and 30 mL of chloroform were added. The mixture was stirred and then allowed to stand, followed by liquid-liquid separation. An extraction operation from the aqueous layer with 10 mL of chloroform was performed twice. The combined chloroform layers were dried over magnesium sulfate, followed by filtration. After removal of the solvent, 0.98 g of RuCl((S,S)—N-Me-Msdpen) (p-cymene) was obtained (Yield: 90.0%).

$^1$H-NMR (CD$_2$Cl$_2$, 400 MHz): δ7.40-7.23 (m, 3H), 7.15-6.96 (m, 7H), 5.58 (d, 1H), 5.42-5.40 (m, 2H), 5.30 (d, 1H), 3.95 (d, 1H), 3.93 (brs, 1H), 3.58 (t, 1H), 3.10 (m, 1H), 2.80 (d, 3H), 2.35 (s, 3H), 2.33 (s, 3H), 1.38-1.35 (m, 6H);

HRMS (ESI) calcd for C$_{26}$H$_{33}$N$_2$O$_2$RuS [M-Cl]$^+$ 539.1306, found 539.1299.

Synthesis Example 18

Synthesis of Ruthenium Complex (RuBF$_4$((S,S)—N-Me-Msdpen) (p-cymene)) (ruthenium complex of general formula (1))

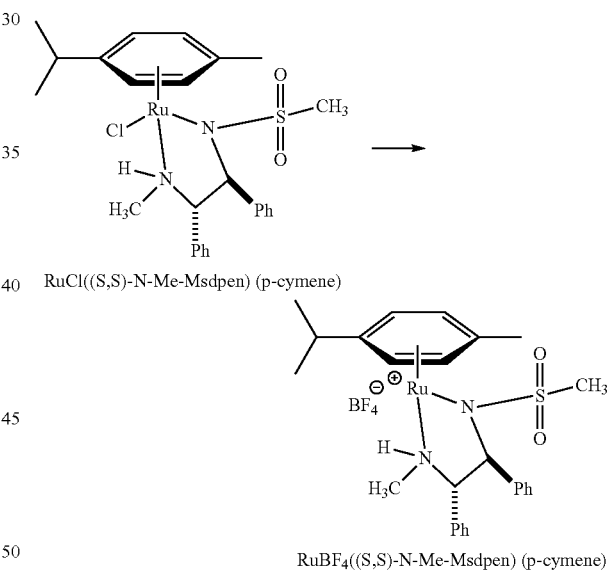

RuCl((S,S)-N-Me-Msdpen) (p-cymene)

RuBF$_4$((S,S)-N-Me-Msdpen) (p-cymene)

In 3 mL of methanol and 15 mL of dichloromethane, 0.88 g (1.53 mmol) of the ruthenium complex, RuCl((S,S)—N-Me-Msdpen) (p-cymene), obtained in Synthesis Example 17 and 0.358 g (1.84 mmol) of AgBF$_4$ were stirred for 2 hours. After the precipitated salt was filtered through Celite, the filtrate was concentrated using an evaporator and dried under reduced pressure. Thus, 0.95 g of RuBF$_4$((S,S)—N-Me-Msdpen) (p-cymene), which is a ruthenium complex of the present invention, was obtained (Yield: 99%).

$^1$H-NMR (CD$_3$OD, 400 MHz): δ 7.40-7.02 (m, 10H), 5.99-5.97 (m, 1H), 5.90-5.86 (m, 2H), 5.77-5.76 (m, 1H), 4.13 (d, 1H), 3.92 (d, 1H), 3.07 (d, 3H), 3.00-2.96 (m, 1H), 2.38 (s, 3H), 2.22 (s, 3H), 1.44-1.29 (m, 6H);

HRMS (ESI) calcd for C$_{26}$H$_{33}$N$_2$O$_2$RuS [M-BF$_4$]+ 539.1306, found 539.1334.

Synthesis Example 19

Synthesis of Ruthenium Complex (RuCl((S,S)—N-Me-Msdpen) (mesitylene)) (ruthenium complex of general formula (2))

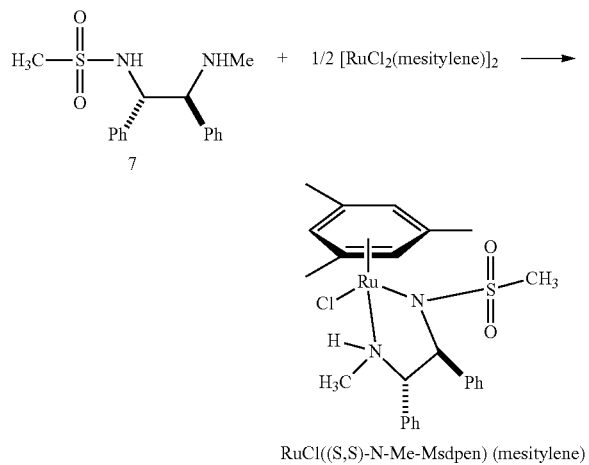

In 15 mL of 2-propanol, 0.6 g (1.90 mmol) of Compound 7 obtained in Synthesis Example 16, 0.555 g (1.90 mmol (in terms of Ru)) of [RuCl$_2$(mesitylene)]$_2$, and 0.385 g (0.54 mL, 3.8 mmol) of triethylamine were dissolved, and the reaction was allowed to proceed at 80° C. for 1.5 hours. After that, the solvent was recovered from the reaction liquid, and 20 mL of water was added, followed by stirring for 10 minutes under ice-cooling. The precipitated crystals were filtered, and then dried under reduced pressure. Thus, 0.60 g of RuCl((S,S)—N-Me-Msdpen) (mesitylene) was obtained (Yield: 56.4.%)

$^1$H-NMR (CD$_2$Cl$_2$, 400 MHz): δ 7.37-7.25 (m, 3H), 7.19-7.00 (m, 7H), 5.27 (s, 3H), 4.00 (d, 1H), 3.90 (brs, 1H), 3.72 (t, 1H), 2.72 (d, 3H), 2.37 (s, 3H), 2.28 (s, 9H);

HRMS (ESI) calcd for C$_{25}$H$_{31}$N$_2$O$_2$RuS [M-Cl]$^+$ 525.1150, found 525.1145.

Synthesis Example 20

Synthesis of Ruthenium Complex (RuBF$_4$((S,S)—N-Me-Msdpen) (mesitylene)) (ruthenium complex of general formula (1))

In 3 mL of methanol and 15 mL of dichloromethane, 0.60 g (1.07 mmol) of the ruthenium complex, RuCl((S,S)—N-Me-Msdpen) (mesitylene), obtained in Synthesis Example 19 and 0.25 g (1.28 mmol) of AgBF$_4$ were stirred for 2 hours. After the precipitated salt was filtered through Celite, the filtrate was concentrated using an evaporator and dried under reduced pressure. Thus, 0.65 g of RuBF$_4$((S,S)—N-Me-Msdpen) (mesitylene), which is a ruthenium complex of the present invention, was obtained (Yield: 99%).

$^1$H-NMR (CD$_3$OD, 400 MHz): δ 7.38-7.10 (m, 10H), 5.70 (s, 3H), 4.52 (d, 1H), 4.20 (d, 1H), 2.99 (d, 3H), 2.35 (s, 3H), 2.17 (s, 9H);

HRMS (ESI) calcd for C$_{25}$H$_{31}$N$_2$O$_2$RuS [M-BF$_4$]$^+$ 525.1150, found 525.1140.

Synthesis Example 21

Synthesis of Ruthenium Complex (RuCl((S,S)—N-Me-Msdpen) (hexamethylbenzene)) (ruthenium complex of general formula (2))

In 10 mL of 2-propanol, 0.4 g (1.31 mmol) of Compound 7 obtained in Synthesis Example 16, 0.439 g (1.31 mmol (in terms of Ru)) of [RuCl$_2$(hexamethylbenzene)]$_2$ and 0.266 g (0.37 mL, 2.63 mmol) of triethylamine were dissolved, and the reaction was allowed to proceed at 80° C. for 1.5 hours. After that, the solvent was recovered from the reaction liquid, and 20 mL of water was added, followed by stirring for 10 minutes under ice-cooling. The precipitated crystals were filtered, and then dried under reduced pressure. Thus, 0.70 g of RuCl((S,S)—N-Me-Msdpen) (hexamethylbenzene) was obtained (Yield: 88.5%).

$^1$H-NMR (CD$_2$Cl$_2$, 400 MHz): δ 7.40-7.10 (m, 10H), 4.08 (d, 1H), 3.72 (t, 1H), 3.70 (brs, 1H), 2.51 (d, 3H), 2.19 (s, 18H);

HRMS (ESI) calcd for C$_{28}$H$_{37}$N$_2$O$_2$RuS [M-Cl]$^+$ 567.1619, found 567.1622.

Synthesis Example 22

Synthesis of Ruthenium Complex (RuBF$_4$ ((S,S)—N-Me-Msdpen) (hexamethylbenzene)) (ruthenium complex of general formula (1))

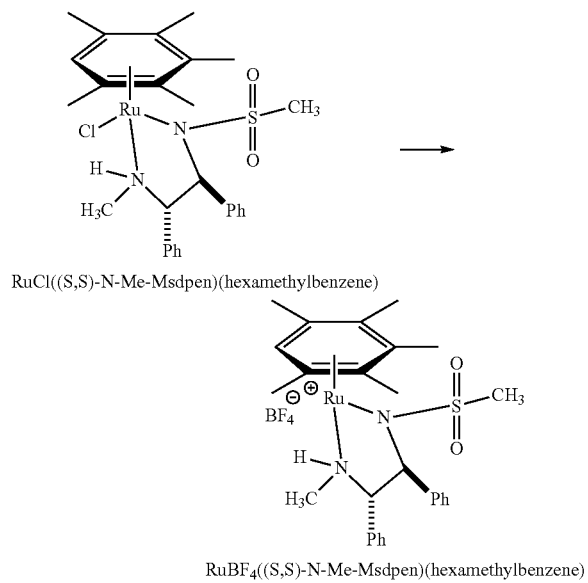

In 3 mL of methanol and 15 mL of dichloromethane, 0.69 g (1.14 mmol) of the ruthenium complex, RuCl((S,S)—N-Me-Msdpen) (hexamethylbenzene), obtained in Synthesis Example 21 and 0.268 g (1.37 mmol) of AgBF$_4$ were stirred for 2 hours. After the precipitated salt was filtered through Celite, the filtrate was concentrated using an evaporator and dried under reduced pressure. Thus, 0.74 g of RuBF$_4$((S,S)—N-Me-Msdpen) (hexamethylbenzene), which is a ruthenium complex of the present invention, was obtained (Yield: 99%).

$^1$H-NMR (CD$_3$OD, 400 MHz): δ 7.40-7.20 (m, 10H), 4.52 (d, 1H), 4.20 (d, 1H), 2.59 (s, 3H), 2.53 (d, 3H), 2.25-2.05 (m, 18H); HRMS (ESI) calcd for C$_2$,H$_{37}$N$_2$O$_2$RuS [M-BF$_4$]$^+$ 567.1619, found 567.1609.

Example 13

Hydrogenation Reaction of 2,5-Dimethylindole using RuBF$_4$ ((S,S)—N-Me-Msdpen) (p-cymene) (asymmetric reduction reaction of the present invention)

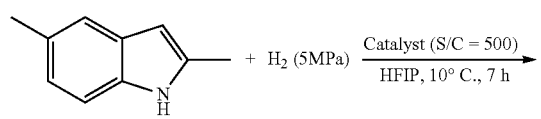

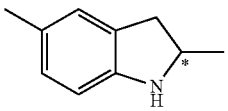

A 50 mL autoclave was charged with 1.3 mg (0.002 mmol, S/C=500) of RuBF$_4$((S,S)—N-Me-Msdpen) (p-cymene) obtained in Synthesis Example 18 serving as a catalyst, 0.145 g (1 mmol) of 2,5-dimethylindole, and 1 mL of HFIP, and the reaction was allowed to proceed at 10° C. for 7 hours under a hydrogen pressure of 5 MPa. The conversion and the optical purity determined by GC analysis were >99.9% conv. (conversion) and 95.8% ee (optical purity).

Example 14

Hydrogenation Reaction of 5-Methoxy-2-methylindole using RuBF$_4$((R,R)—N-Me-Tsdpen) (p-cymene) (asymmetric reduction reaction of the present invention)

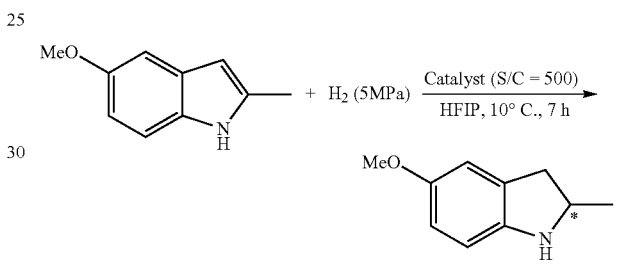

A 50 mL autoclave was charged with 1.4 mg (0.002 mmol, S/C=500) of RuBF$_4$((R,R)—N-Me-Tsdpen) (p-cymene) obtained in Synthesis Example 3 serving as a catalyst, 0.1612 g (1 mmol) of 5-methoxy-2-methylindole, and 1.1 mL of HFIP, and the reaction was allowed to proceed at 10° C. for 7 hours under a hydrogen pressure of 5 MPa. The conversion and the optical purity determined by GC analysis were 98.8% conv. (conversion) and 95.3% ee (optical purity).

Example 15

Hydrogenation Reaction of 5-Methoxy-2-methylindole using RuBF$_4$((S,S)—N-Me-Msdpen) (p-cymene) (asymmetric reduction reaction of the present invention)

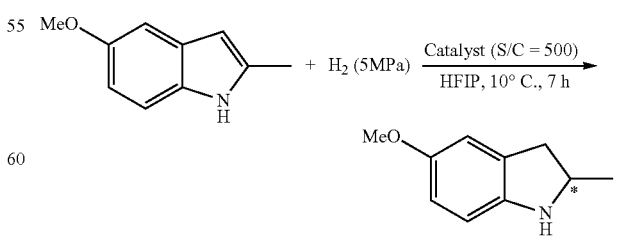

A 50 mL autoclave was charged with 1.3 mg (0.002 mmol, S/C=500) of RuBF$_4$((S,S)—N-Me-Msdpen) (p-cymene) obtained in Synthesis Example 18 serving as a catalyst, 0.1612 g (1 mmol) of 5-methoxy-2-methylindole, and 1 mL of HFIP, and the reaction was allowed to proceed at 10° C. for 7 hours under a hydrogen pressure of 5 MPa. The conversion and the optical purity determined by GC analysis were 99.7% conv. (conversion) and 95.2% ee (optical purity).

Example 16

Hydrogenation Reaction of 5-Chloro-2-methylindole using RuBF$_4$((S,S)—N-Me-Msdpen) (p-cymene) (asymmetric reduction reaction of the present invention)

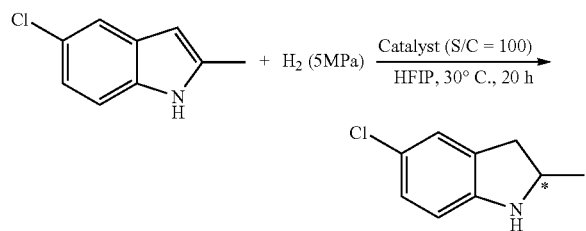

A 50 mL autoclave was charged with 6.3 mg (0.01 mmol, S/C=100) of RuBF$_4$((S,S)—N-Me-Msdpen) (p-cymene) obtained in Synthesis Example 18 serving as a catalyst, 0.1612 g (1 mmol) of 5-chloro-2-methylindole, and 1.2 mL of HFIP, and the reaction was allowed to proceed at 30° C. for 20 hours under a hydrogen pressure of 5 MPa. The conversion and the optical purity determined by GC analysis were 99.1% conv. (conversion) and 94.3% ee (optical purity).

Example 17

Hydrogenation Reaction of 5-Fluoro-2-methylindole using RuBF$_4$((S,S)—N-Me-Msdpen) (p-cymene) (asymmetric reduction reaction of the present invention)

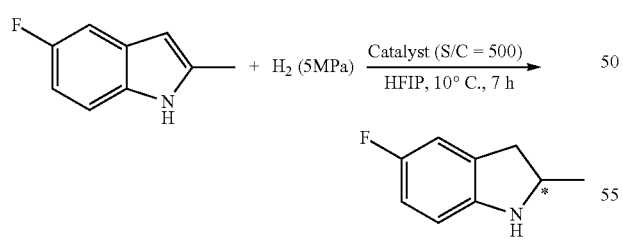

A 50 mL autoclave was charged with 1.3 mg (0.002 mmol, S/C=500) of RuBF$_4$((S,S)—N-Me-Msdpen) (p-cymene) obtained in Synthesis Example 18 serving as a catalyst, 0.149 g (1 mmol) of 5-fluoro-2-methylindole, and 1 mL of HFIP, and the reaction was allowed to proceed at 10° C. for 7 hours under a hydrogen pressure of 5 MPa. The conversion and the optical purity determined by GC analysis were 89.3% conv. (conversion) and 93.9% ee (optical purity).

Example 18

Hydrogenation Reaction of 1,2,3,4-Tetrahydrocarbazole using RuBF$_4$((R,R)—N-Me-Tsdpen) (p-cymene) (asymmetric reduction reaction of the present invention)

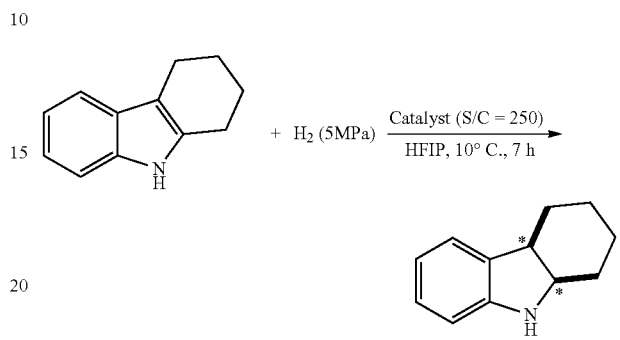

A 50 mL autoclave was charged with 2.8 mg (0.004 mmol, S/C=250) of RuBF$_4$((R,R)—N-Me-Tsdpen) (p-cymene) obtained in Synthesis Example 3 serving as a catalyst, 0.171 g (1 mmol) of 1,2,3,4-tetrahydrocarbazole, and 1.2 mL of HFIP, and the reaction was allowed to proceed at 10° C. for 7 hours under a hydrogen pressure of 5 MPa. The conversion and the optical purity determined by GC analysis were 83.5% conv. (conversion) (only the cis isomer product was formed) and 96.1%. ee (optical purity).

Example 19

Hydrogenation Reaction of 1,2,3,4-Tetrahydrocyclopentaindole using RuBF$_4$((R,R)—N-Me-Tsdpen) (mesitylene) (asymmetric reduction reaction of the present invention)

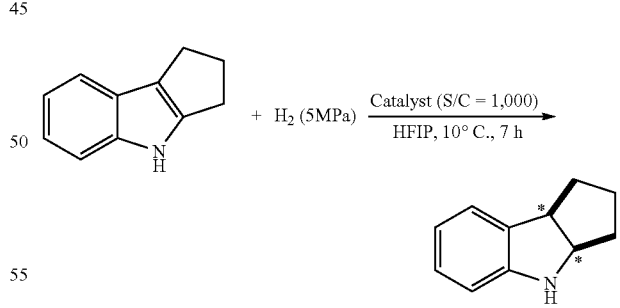

A 100 mL autoclave was charged with 1.4 mg (0.002 mmol, S/C=1,000) of RuBF$_4$((R,R)—N-Me-Tsdpen) (mesitylene) obtained in Synthesis Example 13 serving as a catalyst, 0.314 g (2 mmol) of 1,2,3,4-tetrahydrocyclopentaindole, and 2.2 mL of HFIP, and the reaction was allowed to proceed at 10° C. for 7 hours under a hydrogen pressure of 5 MPa. The conversion and the optical purity determined by GC analysis were 98.5% conv. (conversion) (only the cis isomer product was formed) and 89.7% ee (optical purity).

Example 20

Hydrogenation Reaction of 2,3-Dimethylindole using RuBF$_4$ ((R,R)—N-Me-Tsdpen) (p-cymene) (asymmetric reduction reaction of the present invention)

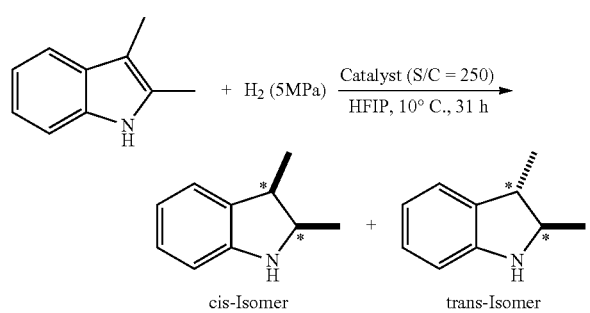

A 50 mL autoclave was charged with 2.8 mg (0.004 mmol, S/C=250) of RuBF$_4$((R,R)—N-Me-Tsdpen) (p-cymene) obtained in Synthesis Example 3 serving as a catalyst, 0.145 g (1 mmol) of 2,3-dimethylindole, and 1.0 mL of HFIP, and the reaction was allowed to proceed at 10° C. for 31 hours under a hydrogen pressure of 5 MPa. The conversion and the optical purity determined by GC analysis were 79.8% conv. (conversion) (cis isomer: 73.3%, trans isomer: 6.5%) and 96.8% ee (cis isomer) and 97.4% ee (trans isomer) (optical purity).

Example 21

Hydrogenation Reaction of 4-Hydroxy-2-methylindole using RuBF$_4$ ((R,R)—N-Me-Tsdpen) (p-cymene) (asymmetric reduction reaction of the present invention)

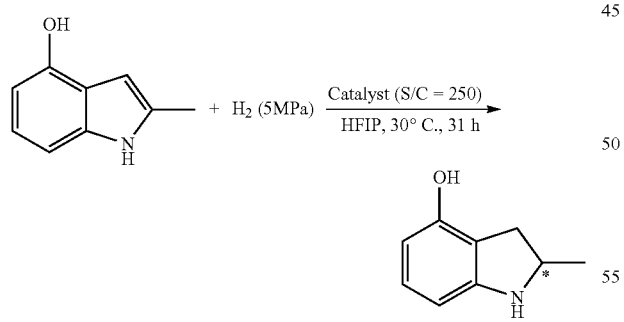

A 50 mL autoclave was charged with 1.4 mg (0.002 mmol, S/C=250) of RuBF$_4$((R,R)—N-Me-Tsdpen) (p-cymene) obtained in Synthesis Example 3 serving as a catalyst, 0.74 g (0.5 mmol) of 4-hydroxy-2-methylindole, and 0.6 mL of HFIP, and the reaction was allowed to proceed at 30° C. for 31 hours under a hydrogen pressure of 5 MPa. The conversion and the optical purity determined by GC analysis were 92.9% conv. (conversion) and 97.6% ee (optical purity).

Example 22

Hydrogenation Reaction of 2-Methylindole using RuBF$_4$((R,R)—N-Me-Tsdpen) (p-cymene) (asymmetric reduction reaction of the present invention)

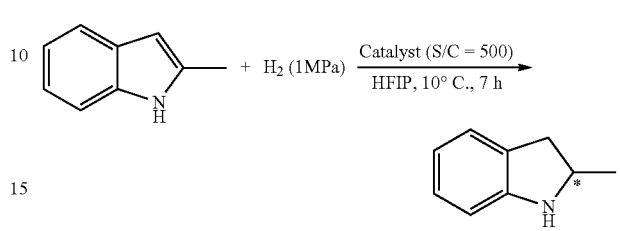

A 50 mL autoclave was charged with 2.1 mg (0.003 mmol, S/C=500) of RuBF$_4$((R,R)—N-Me-Tsdpen) (p-cymene) obtained in Synthesis Example 3 serving as a catalyst, 0.197 g (1.5 mmol) of 2-methylindole, and 1.4 mL of HFIP, and the reaction was allowed to proceed at 10° C. for 7 hours under a hydrogen pressure of 1 MPa. The conversion and the optical purity determined by GC analysis were 96.4% conv. (conversion) and 96.0% ee (optical purity).

Example 23

Hydrogenation Reaction of 2-Methylindole using Iridium Complex (Cp*IrBF$_4$ ((R,R)—N-Me-Tsdpen)) (asymmetric reduction reaction of the present invention)

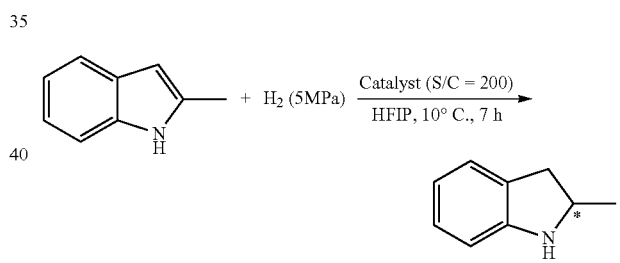

A 50 mL autoclave was charged with 4.0 mg (0.005 mmol, S/C=200) of the iridium complex, (Cp*IrBF$_4$((R,R)—N-Me-Tsdpen)), obtained in Synthesis Example 11 serving as a catalyst, 0.131 g (1.0 mmol) of 2-methylindole, and 0.9 mL of HFIP, and the reaction was allowed to proceed at 10° C. for 7 hours under a hydrogen pressure of 5 MPa. The conversion and the optical purity determined by GC analysis were 99.3% conv. (conversion) and 94.4% ee (optical purity).

Comparative Example 17

Hydrogenation Reaction of 2-Methylindole using Iridium Complex (Cp*IrBF$_4$((R,R)-Tsdpen))

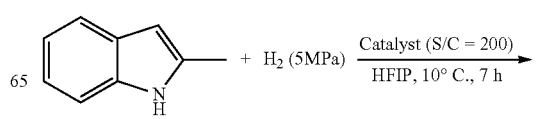

-continued

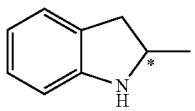

A 50 mL autoclave was charged with 3.9 mg (0.005 mmol, S/C=200) of an iridium complex, (Cp*IrBF$_4$((R,R)-Tsdpen)), serving as a catalyst, 0.131 g (1.0 mmol) of 2-methylindole, and 0.9 mL of HFIP, and the reaction was allowed to proceed at 10° C. for 7 hours under a hydrogen pressure of 5 MPa. The conversion and the optical purity determined by GC analysis were 57.8% conv. (conversion) and 65.7% ee (optical purity).

As described above, it can be seen that the comparison with the conventionally used Cp*IrBF$_4$((R,R)-Tsdpen) complex used in the same catalytic amount showed that both the optical purity and the conversion were improved by the Cp*IrBF$_4$((R,R)—N-Me-Tsdpen) complex of the present invention, and it can be seen that this complex of the present invention has a high activity and a high selectivity.

The invention claimed is:

1. A method for producing an optically active amine, comprising the step of:

reducing an imino group of an imine compound or reducing an unsaturated bond of a heterocyclic compound in the presence of at least one complex selected from the group consisting of a ruthenium complex of the following formula (1), a ruthenium complex of the following formula (2), and an iridium or rhodium complex of the following formula (4) and of hydrogen gas serving as a hydrogen donor:

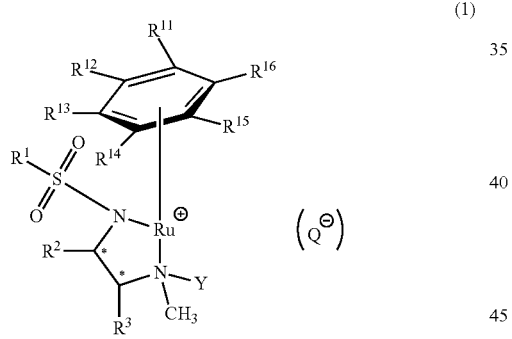

(1)

wherein

* indicates an asymmetric carbon atom,

R$^1$ represents an alkyl group having 1 to 10 carbon atoms, a halogenated alkyl group having 1 to 10 carbon atoms, or an aryl group having 6 to 30 carbon atoms, wherein said aryl group may have one or more substituents selected from the group consisting of an alkyl group having 1 to 10 carbon atoms, a halogenated alkyl group having 1 to 10 carbon atoms, and a halogen atom, R$^2$ and R$^3$ each independently represent an alkyl group having 1 to 10 carbon atoms, a phenyl group, or a cycloalkyl group having 3 to 8 carbon atoms, wherein said phenyl group may have one or more substituents selected from the group consisting of an alkyl group having 1 to 10 carbon atoms, an alkoxy group having 1 to 10 carbon atoms, and a halogen atom, and wherein said cycloalkyl group may have one or more substituents selected from the group consisting of an alkyl group having 1 to 10 carbon atoms, or R$^2$ and R$^3$ form a ring together with the carbon atoms to which R$^2$ and R$^3$ are bonded, Y represents a hydrogen atom or a deuterium atom,

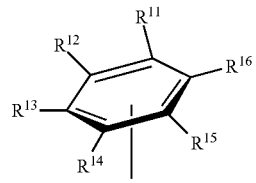

is p-cymene, benzene, mesitylene or hexamethylbenzene, and

Q$^-$ represents a counter anion selected from the group consisting of BF$_4^-$, SbF$_6^-$, CF$_3$COO$^-$, CH$_3$COO$^-$, PF$_6^-$, NO$_3^-$, ClO$_4^-$, SCN$^-$, OCN$^-$, ReO$_4^-$, MoO$_4^-$, BPh$_4^-$, B(C$_6$F$_5$)$_4^-$, and B(3,5-(CF$_3$)$_2$C$_6$F$_3$)$_4^-$;

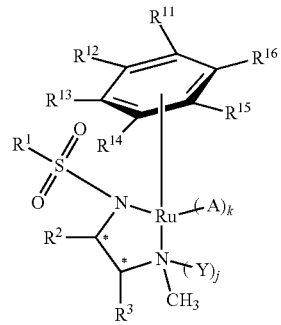

(2)

wherein

* indicates an asymmetric carbon atom,

R$^1$, R$^2$, R$^3$, and Y are as defined above,

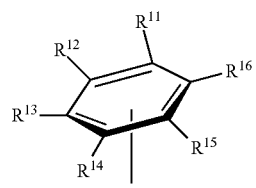

is as defined above,

A represents a trifluoromethanesulfonyloxy group, a p-toluenesulfonyloxy group, a methanesulfonyloxy group, a benzenesulfonyloxy group, a hydrogen atom, a deuterium atom, or a halogen atom, and j and k each represent 0 or 1, provided that j+k is not 1; and

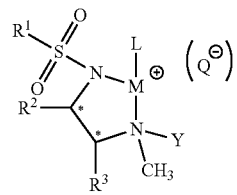

(4)

wherein

* indicates an asymmetric carbon atom,

M represents iridium or rhodium,

L represents a cyclopentadienyl or pentamethylcyclopentadienyl ligand, and

R$^1$, R$^2$, R$^3$, Y, and Q$^-$ are as defined above.

2. A ruthenium complex of formula (1):

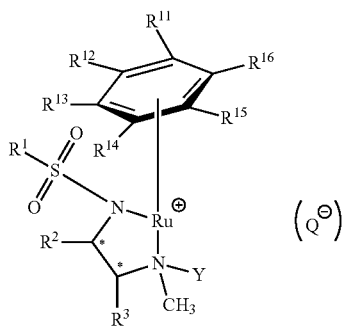
(1)

wherein
* indicates an asymmetric carbon atom,
$R^1$ represents an alkyl group having 1 to 10 carbon atoms, a halogenated alkyl group having 1 to 10 carbon atoms, or an aryl group having 6 to 30 carbon atoms, wherein said aryl group may have one or more substituents selected from the group consisting of an alkyl group having 1 to 10 carbon atoms, a halogenated alkyl group having 1 to 10 carbon atoms, and a halogen atom,
$R^2$ and $R^3$ each independently represent an alkyl group having 1 to 10 carbon atoms, a phenyl group, or a cycloalkyl group having 3 to 8 carbon atoms, wherein said phenyl group may have one or more substituents selected from the group consisting of an alkyl group having 1 to 10 carbon atoms, an alkoxy group having 1 to 10 carbon atoms, and a halogen atom, and wherein said cycloalkyl group may have one or more substituents selected from the group consisting of an alkyl group having 1 to 10 carbon atoms, or $R^2$ and $R^3$ form a ring together with the carbon atoms to which $R^2$ and $R^3$ are bonded,
Y represents a hydrogen atom or a deuterium atom,

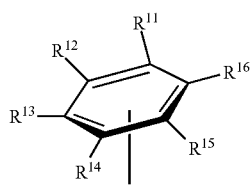

is p-cymene, benzene, mesitylene or hexamethylbenzene, and $Q^-$ represents a counter anion selected from the group consisting of $BF_4^-$, $SbF_6^-$, $CF_3COO^-$, $CH_3COO^-$, $PF_6^-$, $NO_3^-$, $ClO_4^-$, $SCN^-$, $OCN^-$, $ReO_4^-$, $MoO_4^-$, $BPh_4^-$, $B(C_6F_5)_4^-$, and $B(3,5-(CF_3)_2C_6F_3)_4^-$.

3. An iridium or rhodium complex of formula (4):

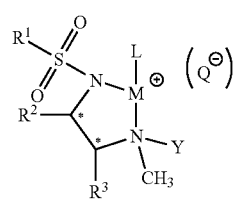
(4)

wherein
* indicates an asymmetric carbon atom,
$R^1$ represents an alkyl group having 1 to 10 carbon atoms, a halogenated alkyl group having 1 to 10 carbon atoms, or an aryl group having 6 to 30 carbon atoms, wherein said aryl group may have one or more substituents selected from the group consisting of an alkyl group having 1 to 10 carbon atoms, a halogenated alkyl group having 1 to 10 carbon atoms, and a halogen atom,
$R^2$ and $R^3$ each independently represent an alkyl group having 1 to 10 carbon atoms, a phenyl group, or a cycloalkyl group having 3 to 8 carbon atoms, wherein said phenyl group may have one or more substituents selected from the group consisting of an alkyl group having 1 to 10 carbon atoms, an alkoxy group having 1 to 10 carbon atoms, and a halogen atom, and wherein said cycloalkyl group may have one or more substituents selected from the group consisting of an alkyl group having 1 to 10 carbon atoms, or $R^2$ and $R^3$ form a ring together with the carbon atoms to which $R^2$ and $R^3$ are bonded,
Y represents a hydrogen atom or a deuterium atom,
M represents iridium or rhodium,
L represents a cyclopentadienyl or pentamethylcyclopentadienyl ligand, and
$Q^-$ represents a counter anion selected from the group consisting of $BF_4^-$, $SbF_6^-$, $CF_3COO^-$, $CH_3COO^-$, $PF_6^-$, $NO_3^-$, $ClO_4^-$, $SCN^-$, $OCN^-$, $ReO_4^-$, $MoO_4^-$, $BPh_4^-$, $B(C_6F_5)_4^-$, and $B(3,5-(CF_3)_2C_6F_3)_4^-$.

* * * * *